(12) United States Patent
Hosoe et al.

(10) Patent No.: US 10,500,158 B2
(45) Date of Patent: Dec. 10, 2019

(54) CATIONIC LIPID

(71) Applicant: Kyowa Hakko Kirin Co., Ltd., Tokyo (JP)

(72) Inventors: Shintaro Hosoe, Tokyo (JP); Tomoyuki Naoi, Tokyo (JP)

(73) Assignee: KYOWA HAKKO KIRIN CO., LTD., Tokyo (JP)

( * ) Notice: Subject to any disclaimer, the term of this patent is extended or adjusted under 35 U.S.C. 154(b) by 134 days.

(21) Appl. No.: 15/322,271

(22) PCT Filed: Jun. 30, 2015

(86) PCT No.: PCT/JP2015/068778
§ 371 (c)(1),
(2) Date: Feb. 6, 2017

(87) PCT Pub. No.: WO2016/002753
PCT Pub. Date: Jan. 7, 2016

(65) Prior Publication Data
US 2017/0224619 A1   Aug. 10, 2017

(30) Foreign Application Priority Data

Jun. 30, 2014   (JP) .................................. 2014-133913

(51) Int. Cl.
*A61K 9/127* (2006.01)
*A61K 31/337* (2006.01)
*A61K 31/713* (2006.01)
*C07D 205/04* (2006.01)
(Continued)

(52) U.S. Cl.
CPC .......... *A61K 9/1272* (2013.01); *A61K 9/0019* (2013.01); *A61K 31/713* (2013.01); *A61K 31/7105* (2013.01); *A61K 47/541* (2017.08); *A61K 47/545* (2017.08); *C07D 205/04* (2013.01); *C07D 207/06* (2013.01); *C12N 2310/14* (2013.01); *C12N 2310/315* (2013.01); *C12N 2310/344* (2013.01); *C12N 2320/32* (2013.01)

(58) Field of Classification Search
CPC .... A61K 31/7088; A61K 47/18; A61K 48/00; A61K 9/127; A61K 31/7105; A61K 31/713; A61K 47/541; A61K 47/545; A61K 9/0019; A61K 9/1272; A61K 9/1271; A61K 9/51; A61K 31/16; C07C 211/21; C07D 205/04; C07D 207/06
USPC ............. 435/375, 458; 514/44 A; 424/278.1, 424/283.1, 400, 450, 451, 490
See application file for complete search history.

(56) References Cited

U.S. PATENT DOCUMENTS

2011/0311582 A1   12/2011 Manoharan et al.
2013/0108685 A1   5/2013 Kuboyama et al.
(Continued)

FOREIGN PATENT DOCUMENTS

JP   2012-508261   4/2012
JP   2013-245190   12/2013
(Continued)

OTHER PUBLICATIONS

Wadsworth, D. H. Journal of Heterocyclic Chemistry, 1966, vol. 3 Issue: 2 p. 230-231. (Year: 1966).*
(Continued)

*Primary Examiner* — Janet L Epps-Smith
(74) *Attorney, Agent, or Firm* — Wenderoth, Lind & Ponack, L.L.P.

(57) ABSTRACT

The present invention provides a cationic lipid represented by the formula (I)

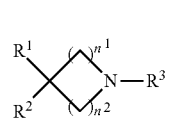

(I)

wherein $R^1$ and $R^2$ each represents alkyl having 8 to 24 carbon atoms or the like; $R^3$ represents a hydrogen atom, alkyl having 1 to 3 carbon atoms, the formula (A)

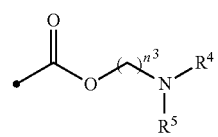

(A)

wherein $R^4$ and $R^5$ each represents a hydrogen atom or the like, and $n^3$ represents an integer from 2 to 6, or the formula (B)

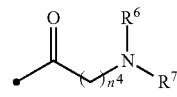

(B)

wherein $R^6$ and $R^7$ each represents a hydrogen atom or the like, and $n^4$ represents an integer from 1 to 6; $n^1$ represents an integer from 0 to 4; and $n^2$ represents an integer from 1 to 4, provided that the case where $n^1$ is 0 and $n^2$ is 1 is excluded, and a composition which contains the cationic lipid and a nucleic acid, or the like.

13 Claims, 1 Drawing Sheet
Specification includes a Sequence Listing.

(51) Int. Cl.
　　　*A61K 9/00*　　　(2006.01)
　　　*A61K 31/7105*　　(2006.01)
　　　*C07D 207/06*　　(2006.01)
　　　*A61K 47/54*　　(2017.01)

(56) References Cited

U.S. PATENT DOCUMENTS

| 2013/0129811 | A1 | 5/2013 | Kuboyama et al. |
| 2014/0039032 | A1* | 2/2014 | Kuboyama ......... A61K 9/0019 |
| | | | 514/44 A |
| 2014/0044755 | A1 | 2/2014 | Naoi et al. |
| 2015/0174261 | A1 | 6/2015 | Kuboyama et al. |

FOREIGN PATENT DOCUMENTS

| WO | WO-0030444 A1 * | 6/2000 | ........... A61K 9/1272 |
| WO | 2010/042877 | 4/2010 | |
| WO | 2010/054401 | 5/2010 | |
| WO | 2011/136368 | 11/2011 | |
| WO | 2011/136369 | 11/2011 | |
| WO | 2012/108397 | 8/2012 | |
| WO | WO-2012108397 A1 * | 8/2012 | ............. A61K 9/127 |
| WO | 2014/007398 | 1/2014 | |
| WO | 2014/013995 | 1/2014 | |

OTHER PUBLICATIONS

International Preliminary Report on Patentability dated Jan. 3, 2017 in corresponding (PCT) International Application No. PCT/JP2015/068778.

International Search Report dated Sep. 15, 2015 in corresponding (PCT) International Application No. PCT/JP2015/068778.

Extended European Search Report dated Jan. 2, 2018 in European Patent Application No. 15814545.8.

* cited by examiner

[Figure 1]
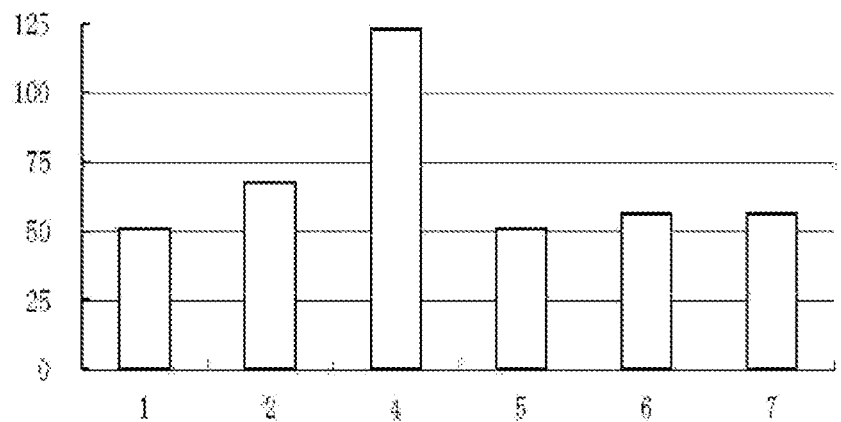
[Figure 2]
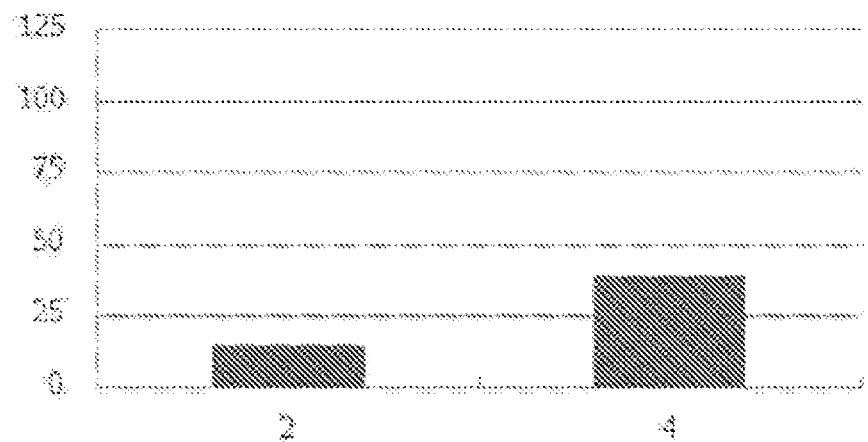
[Figure 3]
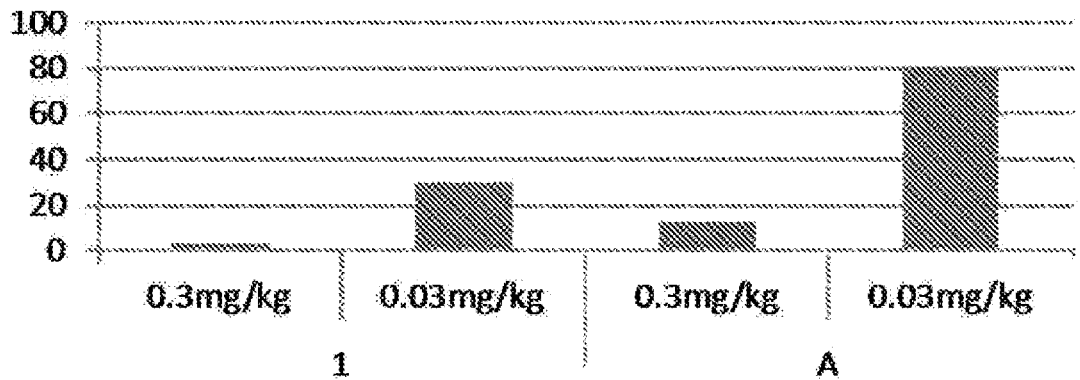

CATIONIC LIPID

TECHNICAL FIELD

The present invention relates to a cationic lipid that facilitates introduction of a nucleic acid, for example, into a cell, a composition containing the cationic lipid, and the like.

BACKGROUND ART

Cationic lipids are amphipathic molecules having a lipophilic region containing one or more hydrocarbon groups, and a hydrophilic region containing at least one positively charged polar head group. Cationic lipids are useful, because cationic lipids facilitate entry of macromolecules such as nucleic acids into the cytoplasm through the cell plasma membrane by forming a positively charged (total charge) complex with macromolecules such as nucleic acids. This process, performed in vitro and in vivo, is known as transfection.

Patent Literatures 1 to 4 disclose cationic lipids and lipid particles containing the lipids, which are advantageous for delivering nucleic acids to cell in vivo, and for using nucleic acid-lipid particle compositions suitable for treatment of a disease. Patent Literature 1 discloses cationic lipids, for example,

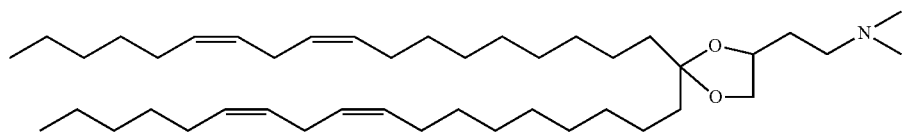 [SMILES: CCCCC/C=C\C/C=C\CCCCCCCCC1(CCCCCCCC/C=C\C/C=C\CCCCC)OCC(CCN(C)C)O1]

2,2-dilinoleyl-4-(2-dimethylaminoethyl)-[1,3]-dioxolane (DLin-KC2-DMA), and the like. Patent Literature 2 discloses cationic lipids, for example,

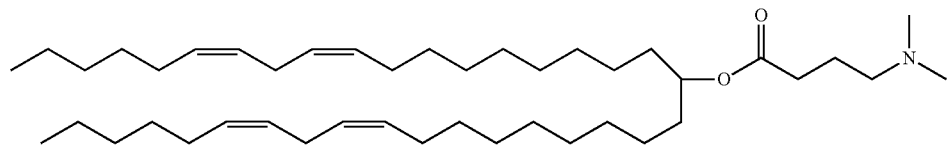 [SMILES: CCCCC/C=C\C/C=C\CCCCCCCCC(CCCCCCCC/C=C\C/C=C\CCCCC)OC(=O)CCCN(C)C]

(6Z,9Z,28Z,31Z)-heptatriaconta-6,9,28,31-tetraen-19-yl 4-(dimethylamino)butanoate (DLin-MC3-DMA), and the like. Patent Literature 3 discloses cationic lipids, for example,

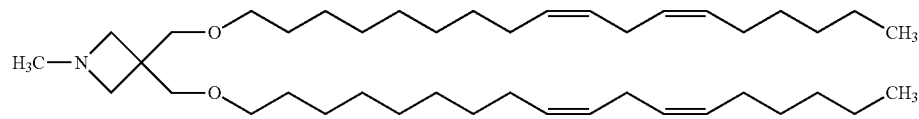 [SMILES: CCCCC/C=C\C/C=C\CCCCCCCCOCC1(COCCCCCCCC/C=C\C/C=C\CCCCC)CN(C)C1]

1-methyl-3,3-bis{[(9Z,12Z)-octadeca-9,12-dien-1-yloxy]methyl}azetidine, and the like. Patent Literature 4 discloses cationic lipids, for example,

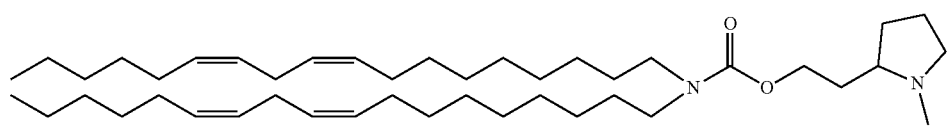 [SMILES: CCCCC/C=C\C/C=C\CCCCCCCCN(CCCCCCCC/C=C\C/C=C\CCCCC)C(=O)OCCC1CCCN1C]

2-(1-methylpyrrolidin-2-yl)ethyl di[(9Z,12Z)-octadeca-9,12-dienyl]carbamate, and the like.

CITATION LIST

Patent Literature

Patent Literature 1: WO 2010/042877
Patent Literature 2: WO 2010/054401
Patent Literature 3: WO 2012/108397
Patent Literature 4: WO 2014/007398

SUMMARY OF THE INVENTION

Technical Problem

An object of the present invention is to provide a cationic lipid that facilitates introduction of a nucleic acid, for example, into a cell, a composition containing the cationic lipid, and the like.

Means for Solving the Problems

The present invention relates to the following (1) to (35):
(1) A cationic lipid represented by the formula (I):

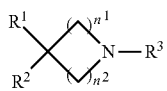

(I)

wherein $R^1$ and $R^2$ are, the same or different, linear or branched alkyl, alkenyl, or alkynyl having 8 to 24 carbon atoms, C7-C20 alkyloxyC1-C3 alkyl, or C7-C20 alkynyloxyC1-C3 alkyl;
$R^3$ is a hydrogen atom, alkyl having 1 to 3 carbon atoms, the formula (A):

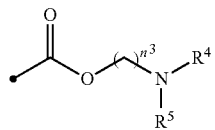

(A)

wherein $R^4$ and $R^5$ are, the same or different, a hydrogen atom or alkyl having 1 to 3 carbon atoms, or $R^4$ and $R^5$, together with the nitrogen atom to which they are attached, may form a nitrogen-containing heterocycle having 2 to 6 carbon atoms and $n^3$ is an integer from 2 to 6, or
the formula (B):

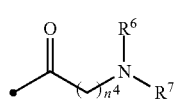

(B)

wherein $R^6$ and $R^7$ are, the same or different, a hydrogen atom or alkyl having 1 to 3 carbon atoms, or $R^6$ and $R^7$, together with the nitrogen atom to which they are attached, may form a nitrogen-containing heterocycle having 2 to 6 carbon atoms, and $n^4$ is an integer from 1 to 6;

$n^1$ is an integer from 0 to 4; and $n^2$ is an integer from 1 to 4, provided that the case where $n^1$ is 0 and $n^2$ is 1 is excluded.
(2) The cationic lipid according to the above described (1), wherein $R^1$ and $R^2$ are, the same or different, selected from the group consisting of tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl.
(3) The cationic lipid according to the above described (1), wherein $R^1$ and $R^2$ are, the same or different, selected from the group consisting of (Z)-hexadec-9-enyl, (Z)-octadec-9-enyl, (9Z,12Z)-octadeca-9,12-dienyl, and (11Z,14Z)-icosa-11,14-dienyl.
(4) The cationic lipid according to any of the above described (1) to (3), wherein $R^3$ is alkyl having 1 to 3 carbon atoms or the formula (A).
(5) The cationic lipid according to any of the above described (1) to (4), wherein $R^1$ and $R^2$ are the same.
(6) The cationic lipid according to any of the above described (1) to (5), wherein $n^1$ is 1, and $n^2$ is an integer from 1 to 3.
(7) The cationic lipid according to any of the above described (1) to (5), wherein both of $n^1$ and $n^2$ are 1.
(8) A cationic lipid represented by the formula (I'):

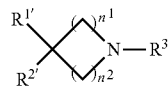

(I')

wherein $R^{1'}$ and $R^{2'}$ are, the same or different, linear or branched alkyl, alkenyl, or alkynyl having 8 to 24 carbon atoms, C7-C20 alkyloxyC1-C3 alkyl, C7-C20 alkenyloxyC1-C3 alkyl, or C7-C20 alkynyloxyC1-C3 alkyl;
$R^3$ is a hydrogen atom, alkyl having 1 to 3 carbon atoms, the formula (A):

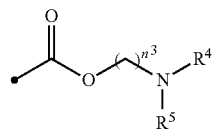

(A)

wherein $R^4$ and $R^5$ are, the same or different, a hydrogen atom or alkyl having 1 to 3 carbon atoms, or $R^4$ and $R^5$, together with the nitrogen atom to which they are attached, may form a nitrogen-containing heterocycle having 2 to 6 carbon atoms, and $n^3$ is an integer from 2 to 6, or
the formula (B):

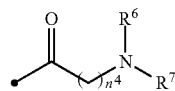

(B)

wherein $R^6$ and $R^7$ are, the same or different, a hydrogen atom or alkyl having 1 to 3 carbon atoms, or $R^6$ and $R^7$, together with the nitrogen atom to which they are attached, may form a nitrogen-containing heterocycle having 2 to 6 carbon atoms, and $n^4$ is an integer from 1 to 6;

$n^1$ is an integer from 0 to 4; and $n^2$ is an integer from 1 to 4, provided that the case where $n^1$ is 0 and $n^2$ is 1 is excluded.

(9) The cationic lipid according to the above described (8), wherein $R^{1'}$ and $R^{2'}$ are, the same or different, selected from the group consisting of tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl.

(10) The cationic lipid according to the above described (8), wherein $R^{1'}$ and $R^{2'}$ are, the same or different, selected from the group consisting of (Z)-hexadec-9-enyl, (Z)-octadec-9-enyl, (9Z,12Z)-octadeca-9,12-dienyl, and (11Z,14Z)-icosa-11,14-dienyl.

(11) The cationic lipid according to any of the above described (8) to (10), wherein $R^3$ is alkyl having 1 to 3 carbon atoms or the formula (A).

(12) The cationic lipid according to any of the above described (8) to (11), wherein $R^{1'}$ and $R^{2'}$ are the same.

(13) The cationic lipid according to any of the above described (8) to (12), wherein $n^1$ is 1, and $n^2$ is an integer from 1 to 3.

(14) The cationic lipid according to any of the above described (8) to (12), wherein both of $n^1$ and $n^2$ are 1.

(15) A cationic lipid represented by the formula (I″):

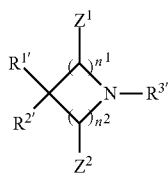

(I″)

wherein $R^{1'}$ and $R^{2'}$ are, the same or different, linear or branched alkyl, alkenyl, or alkynyl having 8 to 24 carbon atoms, C7-C20 alkyloxyC1-C3 alkyl, C7-C20 alkenyloxyC1-C3 alkyl, or C7-C20 alkynyloxyC1-C3 alkyl;

$R^{3'}$ is a hydrogen atom, alkyl having 1 to 3 carbon atoms, hydroxyC2-C4 alkyl, C1-C3 dialkylamino-C2-C4 alkyl, the formula (A):

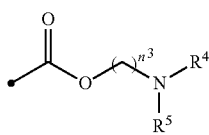

(A)

wherein $R^4$ and $R^5$ are, the same or different, a hydrogen atom or alkyl having 1 to 3 carbon atoms, or $R^4$ and $R^5$, together with the nitrogen atom to which they are attached, may form a nitrogen-containing heterocycle having 2 to 6 carbon atoms, and $n^3$ is an integer from 2 to 6, or the formula (B):

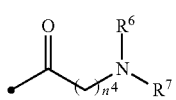

(B)

wherein $R^6$ and $R^7$ are, the same or different, a hydrogen atom or alkyl having 1 to 3 carbon atoms, or $R^6$ and $R^7$, together with the nitrogen atom to which they are attached, may form a nitrogen-containing heterocycle having 2 to 6 carbon atoms, and $n^4$ is an integer from 1 to 6;

$n^{31}$ is an integer from 0 to 4; $n^2$ is an integer from 1 to 4, provided that the case where $n^1$ is 0 and $n^2$ is 1 is excluded;

$Z^1$ is, independently for each carbon atom bonded thereto, a hydrogen atom or alkyl having 1 to 3 carbon atoms; and $Z^2$ is, independently for each carbon atom bonded thereto, a hydrogen atom or alkyl having 1 to 3 carbon atoms.

(16) The cationic lipid according to the above described (15), wherein $R^{1'}$ and $R^{2'}$ are, the same or different, selected from the group consisting of tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl.

(17) The cationic lipid according to the above described (15), wherein $R^{1'}$ and $R^{2'}$ are, the same or different, selected from the group consisting of (Z)-hexadec-9-enyl, (Z)-octadec-9-enyl, (9Z,12Z)-octadeca-9,12-dienyl, and (11Z,14Z)-icosa-11,14-dienyl.

(18) The cationic lipid according to any of the above described (15) to (17), wherein $R^{3'}$ is alkyl having 1 to 3 carbon atoms or the formula (A).

(19) The cationic lipid according to any of the above described (15) to (18), wherein $R^{1'}$ and $R^{2'}$ are the same.

(20) The cationic lipid according to any of the above described (15) to (19), wherein $n^1$ is 1, and $n^2$ is an integer from 1 to 3.

(21) The cationic lipid according to any of the above described (15) to (19), wherein both of $n^1$ and $n^2$ are 1.

(22) A composition comprising the cationic lipid according to any of the above described (1) to (21) and a nucleic acid.

(23) The composition according to the above described (22), wherein the cationic lipid and the nucleic acid form a complex, or the cationic lipid combined with a neutral lipid and/or a polymer and the nucleic acid form a complex.

(24) The composition according to the above described (22), wherein the cationic lipid and the nucleic acid form a complex, or the cationic lipid combined with a neutral lipid and/or a polymer and the nucleic acid form a complex, and the composition contains a lipid membrane with which the complex is enclosed.

(25) The composition according to any of the above described (22) to (24), wherein the nucleic acid is a nucleic acid having a silencing effect on a target gene through the use of RNA interference (RNAi).

(26) The composition according to the above described (25), wherein the target gene is a gene expressed in the liver, the lung, the kidney, or the spleen.

(27) A method for introducing the nucleic acid into a cell using a composition according to any of the above described (22) to (26).

(28) The method according to the above described (27), wherein the cell is a cell that resides in the liver, the lung, the kidney, or the spleen of a mammal.

(29) The method according to the above described (27) or (28), wherein the method for introduction into a cell is a method for introduction into a cell by the intravenous administration of the composition.

(30) A method for treating a disease related to the liver, the lung, the kidney, or the spleen, comprising the step of administering a composition according to the above described (26) to a mammal.
(31) The method according to the above described (30), wherein the administration method is intravenous administration.
(32) A medicament for use in the treatment of a disease, comprising a composition according to the above described (25).
(33) The medicament according to the above described (32), wherein the medicament is for intravenous administration.
(34) A therapeutic agent for a disease related to the liver, the lung, the kidney, or the spleen, comprising a composition according to the above described (26).
(35) The therapeutic agent for a disease related to the liver, the lung, the kidney, or the spleen according to the above described (34), wherein the therapeutic agent is for intravenous administration.

Advantage of Invention

A composition containing the cationic lipid of the present invention and a nucleic acid can easily introduce the nucleic acid, for example, into a cell, by its administration to a mammal or the like.

BRIEF DESCRIPTION OF THE DRAWINGS

FIG. 1 shows the concentration of factor VII protein in plasma 48 hours after administration of each of preparations (preparations obtained by using compounds 1, 2, and 4 to 7, respectively) obtained in Examples 21 and 22 in an amount corresponding to 0.03 mg/kg of siRNA to mice. The ordinate depicts the relative value of the concentration of factor VII protein in plasma with that in a physiological saline administration group defined as 100. The abscissa depicts compound No.

FIG. 2 shows the concentration of factor VII protein in plasma 48 hours after administration of each of preparations (preparations obtained by using compounds 2 and 4, respectively) obtained in Example 22 in an amount corresponding to 0.3 mg/kg of siRNA to mice. The ordinate depicts the relative value of the concentration of factor VII protein in plasma with that in a physiological saline administration group defined as 100. The abscissa depicts compound No.

FIG. 3 shows the concentration of factor VII protein in plasma 48 hours after administration of each of a preparation (preparation obtained by using compound 1) obtained in Example 23 and a preparation (preparation obtained by using compound A) obtained in Comparative Example 1 in amounts corresponding to 0.3 mg/kg and 0.03 mg/kg of siRNA to mice. The ordinate depicts the relative value of the concentration of factor VII protein in plasma with that in a physiological saline administration group defined as 100. The abscissa depicts compound No.

MODE FOR CARRYING OUT THE INVENTION

The cationic lipid of the present invention is a cationic lipid represented by the formula (I):

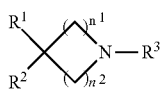

(I)

wherein $R^1$ and $R^2$ are, the same or different, linear or branched alkyl, alkenyl, or alkynyl having 8 to 24 carbon atoms, C7-C20 alkyloxyC1-C3 alkyl, or C7-C20 alkynyloxyC1-C3 alkyl;

$R^3$ is a hydrogen atom, alkyl having 1 to 3 carbon atoms, the formula (A):

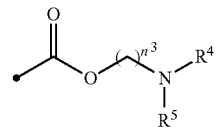

(A)

wherein $R^4$ and $R^5$ are, the same or different, a hydrogen atom or alkyl having 1 to 3 carbon atoms, or $R^4$ and $R^5$, together with the nitrogen atom to which they are attached, may form a nitrogen-containing heterocycle having 2 to 6 carbon atoms, and $n^3$ is an integer from 2 to 6, or the formula (B):

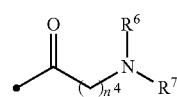

(B)

wherein $R^6$ and $R^7$ are, the same or different, a hydrogen atom or alkyl having 1 to 3 carbon atoms, or $R^6$ and $R^7$, together with the nitrogen atom to which they are attached, may form a nitrogen-containing heterocycle having 2 to 6 carbon atoms, and $n^4$ is an integer from 1 to 6;

$n^1$ is an integer from 0 to 4; and $n^2$ is an integer from 1 to 4, provided that the case where $n^1$ is 0 and $n^2$ is 1 is excluded, or a cationic lipid represented by the formula (I'):

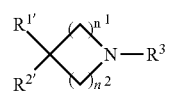

(I')

wherein $R^{1'}$ and $R^{2'}$ are, the same or different, linear or branched alkyl, alkenyl, or alkynyl having 8 to 24 carbon atoms, C7-C20 alkyloxyC1-C3 alkyl, C7-C20 alkenyloxyC1-C3 alkyl, or C7-C20 alkynyloxyC1-C3 alkyl;

$R^3$ is a hydrogen atom, alkyl having 1 to 3 carbon atoms, the formula (A):

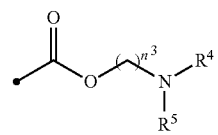

(A)

wherein $R^4$ and $R^5$ are, the same or different, a hydrogen atom or alkyl having 1 to 3 carbon atoms, or $R^4$ and $R^5$, together with the nitrogen atom to which they are attached, may form a nitrogen-containing heterocycle having 2 to 6 carbon atoms, and $n^3$ is an integer from 2 to 6, or
the formula (B):

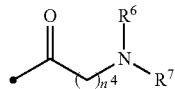  (B)

wherein $R^6$ and $R^7$ are, the same or different, a hydrogen atom or alkyl having 1 to 3 carbon atoms, or $R^6$ and $R^7$, together with the nitrogen atom to which they are attached, may form a nitrogen-containing heterocycle having 2 to 6 carbon atoms, and $n^4$ is an integer from 1 to 6;

$n^1$ is an integer from 0 to 4; and $n^2$ is an integer from 1 to 4, provided that the case where $n^1$ is 0 and $n^2$ is 1 is excluded, or a cationic lipid represented by the formula (I''):

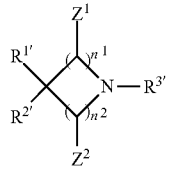  (I'')

wherein $R^{1'}$ and $R^{2'}$ are, the same or different, linear or branched alkyl, alkenyl, or alkynyl having 8 to 24 carbon atoms, C7-C20 alkyloxyC1-C3 alkyl, C7-C20 alkenyloxyC1-C3 alkyl, or C7-C20 alkynyloxyC1-C3 alkyl;

$R^{3'}$ is a hydrogen atom, alkyl having 1 to 3 carbon atoms, hydroxyC2-C4 alkyl, C1-C3 dialkylamino-C2-C4 alkyl, the formula (A):

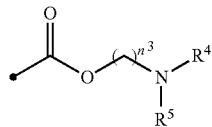  (A)

wherein $R^4$ and $R^5$ are, the same or different, a hydrogen atom or alkyl having 1 to 3 carbon atoms, or $R^4$ and $R^5$, together with the nitrogen atom to which they are attached, may form a nitrogen-containing heterocycle having 2 to 6 carbon atoms, and $n^3$ is an integer from 2 to 6, or
the formula (B):

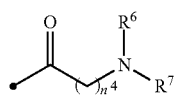  (B)

wherein $R^6$ and $R^7$ are, the same or different, a hydrogen atom or alkyl having 1 to 3 carbon atoms, or $R^6$ and $R^7$, together with the nitrogen atom to which they are attached, may form a nitrogen-containing heterocycle having 2 to 6 carbon atoms, and $n^4$ is an integer from 1 to 6;

$n^1$ is an integer from 0 to 4; $n^2$ is an integer from 1 to 4, provided that the case where $n^1$ is 0 and $n^2$ is 1 is excluded;

$Z^1$ is, independently for each carbon atom bonded thereto, a hydrogen atom or alkyl having 1 to 3 carbon atoms; and $Z^2$ is, independently for each carbon atom bonded thereto, a hydrogen atom or alkyl having 1 to 3 carbon atoms.

Hereinafter, the compound represented by the formula (I) is also referred to as compound (I); the compound represented by the formula (I') is also referred to as compound (I'); and the compound represented by the formula (I'') is also referred to as compound (I''). The same holds true for compounds of other formula numbers.

Examples of the linear or branched alkyl having 8 to 24 carbon atoms include octyl, decyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, henicosyl, docosyl, tricosyl, tetracosyl, or the like. Examples thereof preferably include decyl, dodecyl, tetradecyl, hexadecyl, octadecyl, icosyl or the like, and more preferably include tetradecyl and hexadecyl.

The linear or branched alkenyl having 8 to 24 carbon atoms can be any linear or branched alkenyl having 8 to 24 carbon atoms and containing one or more double bonds. Examples thereof include (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl, (Z)-docos-13-enyl, or the like. Examples thereof preferably include (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, (Z)-docos-13-enyl, or the like.

The linear or branched alkynyl having 8 to 24 carbon atoms can be any linear or branched alkynyl having 8 to 24 carbon atoms and containing one or more triple bonds. Examples thereof include dodec-11-ynyl, tetradec-6-ynyl, hexadec-7-ynyl, hexadeca-5,7-diynyl, octadec-9-ynyl, or the like.

Examples of the C7-C20 alkyl moiety in C7-C20 alkyloxyC1-C3 alkyl include heptyl, octyl, decyl, dodecyl, tridecyl, tetradecyl, 2,6,10-trimethylundecyl, pentadecyl, 3,7,11-trimethyldodecyl, hexadecyl, heptadecyl, octadecyl, 6,10,14-trimethylpentadecan-2-yl, nonadecyl, 2,6,10,14-tetramethylpentadecyl, icosyl, 3,7,11,15-tetramethylhexadecyl, or the like. Examples of the C1-C3 alkyl moiety include alkylene corresponding to methyl, ethyl, propyl, or the like.

Examples of the C7-C20 alkenyl moiety in C7-C20 alkenyloxyC1-C3 alkyl include (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, 3,7,11-trimethyldodeca-2,6,10-trienyl, 3,7,11,15-tetramethylhexadec-2-enyl, or the like, and preferably include (Z)-hexadec-9-enyl, (Z)-octadec-6-enyl, (Z)-octadec-9-enyl, (9Z,12Z)-octadeca-9,12-dienyl, (Z)-icos-11-enyl, (11Z,14Z)-icosa-11,14-dienyl, or the like. Examples of the C1-C3 alkyl moiety include alkylene corresponding to methyl, ethyl, propyl, or the like.

Examples of the C7-C20 alkynyl moiety in C7-C20 alkynyloxyC1-C3 alkyl include dodec-11-ynyl, tetradec-6-ynyl, hexadec-7-ynyl, hexadeca-5,7-diynyl, octadec-9-ynyl, or the like. Examples of the C1-C3 alkyl moiety include methyl, ethyl, propyl, or the like.

In the present invention, a group having a cyclopropane ring formed by adding formally a methylene biradical to a double bond of the linear or branched alkenyl having 8 to 24 carbon atoms is also included in the linear or branched alkenyl having 8 to 24 carbon atoms. The same holds true for the C7-C20 alkenyl moiety in C7-C20 alkenyloxyC1-C3 alkyl. Examples thereof include the following groups having a cyclopropane ring:

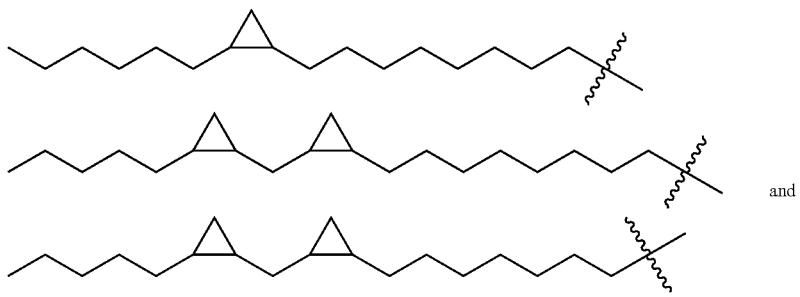

which correspond to (Z)-hexadec-9-enyl, (9Z,12Z)-octadeca-9,12-dienyl, (8Z,11Z)-heptadeca-8,11-dienyl, or the like.

Examples of the alkyl having 1 to 3 carbon atoms include methyl, ethyl, propyl, isopropyl, cyclopropyl, or the like.

Examples of the C2-C4 alkyl moiety in hydroxyC2-C4 alkyl include alkylene corresponding to ethyl, propyl, butyl, or the like.

Examples of the C1-C3 alkyl moieties in C1-C3 dialkylamino-C2-C4 alkyl include methyl, ethyl, propyl, or the like. The two C1-C3 alkyl moieties may be the same or different. Examples of the C2-C4 alkyl moiety in C1-C3 dialkylamino-C2-C4 alkyl include alkylene corresponding to ethyl, propyl, butyl, or the like.

Examples of the nitrogen-containing heterocycle having 2 to 6 carbon atoms include an aziridine ring, an azetidine ring, a pyrrolidine ring, a piperidine ring, a piperazine ring, an azepane ring, or the like.

$R^1$ and $R^2$ are, the same or different, more preferably linear or branched alkyl or alkenyl having 8 to 24 carbon atoms or C7-C20 alkyloxyC1-C3 alkyl. $R^1$ and $R^2$ are, the same or different, further preferably linear alkenyl having 8 to 24 carbon atoms. Also more preferably, $R^1$ and $R^2$ are the same. In this case, linear or branched alkyl, alkenyl, or alkynyl having 12 to 24 carbon atoms is more preferred, and linear alkenyl having 12 to 24 carbon atoms is further preferred. $R^{1'}$ and $R^{2'}$ are, the same or different, more preferably linear or branched alkyl or alkenyl having 8 to 24 carbon atoms, C7-C20 alkyloxyC1-C3 alkyl, or C7-C20 alkenyloxyC1-C3 alkyl. $R^{1'}$ and $R^{2'}$ are, the same or different, further preferably linear alkenyl having 8 to 24 carbon atoms. Also more preferably, $R^{1'}$ and $R^{2'}$ are the same. In this case, linear or branched alkyl, alkenyl, or alkynyl having 12 to 24 carbon atoms is more preferred, and linear alkenyl having 12 to 24 carbon atoms is further preferred.

When $R^1$ and $R^2$ or $R^{1'}$ and $R^{2'}$ are different, $R^1$ or $R^{1'}$ is linear or branched alkyl, alkenyl, or alkynyl having 16 to 24 carbon atoms, and $R^2$ or $R^{2'}$ is linear or branched alkyl, alkenyl, or alkynyl having 8 to 12 carbon atoms, according to a preferred embodiment of the present invention. In this case, more preferably, $R^1$ or $R^{1'}$ is linear alkenyl having 16 to 24 carbon atoms, and $R^2$ or $R^{2'}$ is linear alkyl having 8 to 12 carbon atoms. Most preferably, $R^1$ or $R^{1'}$ is (Z)-octadec-9-enyl or (9Z,12Z)-octadeca-9,12-dienyl, and $R^2$ or $R^{2'}$ is octyl, decyl, or dodecyl.

When $R^1$ and $R^2$ or $R^{1'}$ and $R^{2'}$ are, the same or different, linear or branched alkyl or alkenyl having 8 to 24 carbon atoms, $R^1$ and $R^2$ or $R^{1'}$ and $R^{2'}$ are, the same or different, preferably decyl, dodecyl, tetradecyl, hexadecyl, octadecyl, icosyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, or (Z)-docos-13-enyl. $R^1$ and $R^2$ or $R^{1'}$ and $R^{2'}$ are, the same or different, more preferably tetradecyl, hexadecyl, (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, or (Z)-docos-13-enyl.

$R^3$ or $R^{3'}$ is preferably alkyl having 1 to 3 carbon atoms or the above formula (A), more preferably methyl, ethyl, propyl or cyclopropyl, further preferably methyl or ethyl, most preferably methyl. When $R^3$ is the formula (A), $R^4$ and $R^5$ are, the same or different, preferably a hydrogen atom or alkyl having 1 to 3 carbon atoms. When $R^3$ is the formula (B), $R^6$ and $R^7$ are, the same or different, preferably a hydrogen atom or alkyl having 1 to 3 carbon atoms.

Preferred examples of the nitrogen-containing heterocycle having 2 to 6 carbon atoms, formed by $R^4$ and $R^5$ together with the nitrogen atom to which they are attached include an azetidine ring, a pyrrolidine ring, a piperidine ring, and an azepane ring.

When $R^4$ and $R^5$ do not together form the nitrogen-containing heterocycle having 2 to 6 carbon atoms, $R^5$ is preferably methyl or ethyl, more preferably methyl. Most preferably, each of $R^4$ and $R^5$ is methyl. When $R^4$ and $R^5$ together form the nitrogen-containing heterocycle having 2 to 6 carbon atoms, $R^4$ and $R^5$ preferably form a pyrrolidine ring or a piperidine ring.

$n^3$ is preferably an integer from 2 to 4, more preferably 3.

When $R^6$ and $R^7$ in the above formula (B) do not together form the nitrogen-containing heterocycle having 2 to 6 carbon atoms, $R^7$ is preferably methyl or ethyl, more preferably methyl. Most preferably, each of $R^6$ and $R^7$ is methyl. When $R^6$ and $R^7$ together form the nitrogen-containing heterocycle having 2 to 6 carbon atoms, $R^6$ and $R^7$ preferably form a pyrrolidine ring or a piperidine ring.

$n^4$ is preferably an integer from 2 to 4, more preferably 3.

$n^1$ is preferably 1. In this case, $n^2$ is preferably an integer from 1 to 3, more preferably 1.

$Z^1$ is, independently for each carbon atom bonded thereto, preferably a hydrogen atom or alkyl having 1 to 3 carbon atoms, more preferably a hydrogen atom or methyl, further preferably a hydrogen atom. In this context, the term "independently for each carbon atom bonded thereto" means that when two or more $Z^1$ moieties are present in the formula (I″), these $Z^1$ moieties are the same or different and can each be selected from a hydrogen atom and alkyl having 1 to 3 carbon atoms, depending on the carbon atom bonded to each $Z^1$. For example, when two $Z^1$ moieties are present in the formula (I″), the term not only means that the same substituents can be selected as these two $Z^1$ moieties, but means that the case where one of the $Z^1$ moieties is a hydrogen atom and the other $Z^1$ moiety is alkyl having 1 to 3 carbon atoms is also included.

$Z^2$ is, independently for each carbon atom bonded thereto, preferably a hydrogen atom or alkyl having 1 to 3 carbon atoms, more preferably a hydrogen atom or methyl, further preferably a hydrogen atom. In this context, the term "independently for each carbon atom bonded thereto" means that when two or more $Z^2$ moieties are present in the formula (I″), these $Z^2$ moieties are the same or different and can each be selected from a hydrogen atom and alkyl having 1 to 3 carbon atoms, depending on the carbon atom bonded to each $Z^2$. For example, when two $Z^2$ moieties are present in the formula (I″), the term not only means that the same substituents can be selected as these two $Z^2$ moieties, but means that the case where one of the $Z^2$ moieties is a hydrogen atom and the other $Z^2$ moiety is alkyl having 1 to 3 carbon atoms is also included.

When both of $n^1$ and $n^2$ are 1, $Z^1$ and $Z^2$ are, the same or different, preferably a hydrogen atom or methyl, each more preferably, $Z^1$ is a hydrogen atom or methyl, and $Z^2$ is a hydrogen atom, and most preferably, both of $Z^1$ and $Z^2$ are hydrogen atoms.

Next, methods for producing the cationic lipid of the present invention will be described. In the production methods shown below, if defined groups react under conditions of the production methods or are unsuitable for carrying out the production methods, the desired compounds can be produced by use of introduction and removal methods of protective groups commonly used in organic synthetic chemistry [e.g., methods described in Protective Groups in Organic Synthesis, third edition, T. W. Greene, John Wiley & Sons Inc. (1999) or the like] or the like. If necessary, the order of reaction steps including substituent introduction or the like may be changed.

Production Method 1

Compound (I) wherein both of $n^1$ and $n^2$ are 1, and $R^3$ is a hydrogen atom or alkyl having 1 to 3 carbon atoms (compound (Ia)) can be produced by a method given below. Compound (I') wherein both of $n^1$ and $n^2$ are 1, and $R^3$ is a hydrogen atom or alkyl having 1 to 3 carbon atoms can also be similarly produced by the method given below. In addition, compound (I″) wherein both of $n^1$ and $n^2$ are 1, both of $Z^1$ and $Z^2$ are hydrogen atoms, and $R^{3'}$ is a hydrogen atom, alkyl having 1 to 3 carbon atoms, hydroxyC2-C4 alkyl, or C1-C3 dialkylamino-C2-C4 alkyl can also be similarly produced by the method given below.

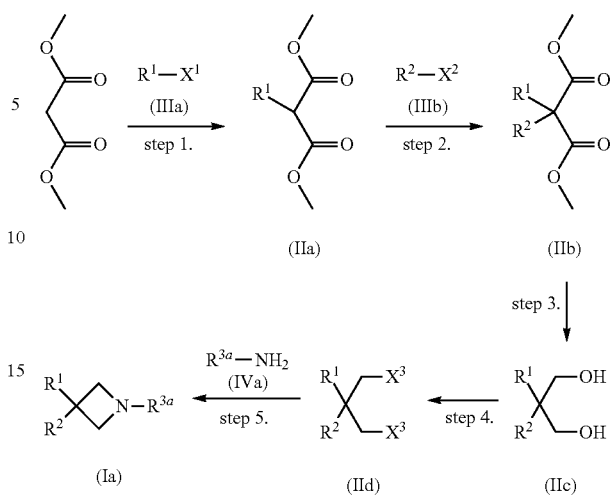

wherein $R^1$ and $R^2$ are each as defined above, $R^{3a}$ is a hydrogen atom or alkyl having 1 to 3 carbon atoms as defined in the alkyl having 1 to 3 carbon atoms represented by $R^3$, and $X^1$, $X^2$ and $X^3$ are, the same or different, a leaving group such as a chlorine atom, a bromine atom, an iodine atom, trifluoromethanesulfonyloxy, methanesulfonyloxy, benzenesulfonyloxy, or p-toluenesulfonyloxy.

Steps 1 and 2

Compound (IIa) can be produced by reacting dimethyl malonate with compound (IIIa) at a temperature between room temperature and 200° C. for 5 minutes to 100 hours in the presence of 1 to 10 equivalents of a base without a solvent or in a solvent. Further, compound (IIb) can be produced by reacting compound (IIa) with compound (IIIb) at a temperature between room temperature and 200° C. for 5 minutes to 100 hours in the presence of 1 to 10 equivalents of a base without a solvent or in a solvent.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, pyridine, or the like. These solvents can be used singly or as a mixture.

Examples of the base include potassium carbonate, cesium carbonate, potassium hydroxide, sodium hydroxide, sodium methoxide, potassium tert-butoxide, sodium hydride, triethylamine, diisopropylethylamine, N-methylmorpholine, pyridine, 1,8-diazabicyclo[5.4.0]-7-undecene (DBU), or the like.

Compound (IIIa) and compound (IIIb) can each be obtained as a commercially available product or by a method known in the art (e.g., "The Fifth Series of Experimental Chemistry 13, Synthesis of Organic Compound I", 5th edition, p. 374, Maruzen Co., Ltd. (2005)) or a method equivalent thereto, or a production method mentioned later.

When $R^1$ and $R^2$ are the same, compound (IIb) can be obtained by using 2 equivalents or more of compound (IIIa) in step 1.

Dimethyl malonate can be obtained as a commercially available product.

Step 3

Compound (IIc) can be produced by reacting compound (IIb) with 4 equivalents to a large excess of a hydride reducing agent at a temperature between −20° C. and 150° C. for 5 minutes to 72 hours, if necessary in the presence of a catalytic amount to 10 equivalents of an additive, in a solvent. In this context, the catalytic amount refers to 0.01 equivalents to 0.5 equivalents.

Examples of the hydride reducing agent include lithium aluminum hydride, lithium borohydride, lithium triethylborohydride, diisobutyl aluminum hydride, sodium bis(2-methoxyethoxy)aluminum hydride, or the like.

Examples of the solvent include toluene, dichloromethane, diethyl ether, tetrahydrofuran, 1,2-dimethoxyethane, 1,4-dioxane, or the like. These solvents can be used singly or as a mixture.

Aluminum chloride, cerium chloride, titanium tetrachloride, titanium tetraisopropoxide, or the like can be used as the additive.

Step 4

Compound (IId) can be produced by reacting compound (IIc) with 2 equivalents or more of a halogenation reagent or a pseudohalogenation reagent at a temperature between −20° C. and 150° C. for 5 minutes to 100 hours in the presence of, if necessary, preferably 1 to 10 equivalents of a base and, if necessary, preferably 1 to 10 equivalents of an additive, without a solvent or in a solvent.

Examples of the halogenation reagent or the pseudohalogenation reagent include thionyl chloride, sulfuryl chloride, phosphorus trichloride, phosphorus pentachloride, phosphorus oxychloride, phosphorus tribromide, hydrogen bromide, hydrogen iodide, mesylic anhydride, mesyl chloride, tosylic anhydride, benzenesulfonyl chloride, benzenesulfonic anhydride, tosyl chloride, trifluoromethanesulfonic anhydride, or the like.

Examples of the solvent include those listed in step 3.

Examples of the base include pyridine, 2,6-lutidine, 2,4,6-collidine, triethylamine, N,N-diisopropylethylamine, or the like.

Examples of the additive include sodium chloride, sodium bromide, lithium bromide, lithium chloride, or the like.

Step 5

Compound (Ia) can be produced by reacting compound (IId) with 1 equivalent to a large excess of compound (IVa) at a temperature between room temperature and 200° C. for 5 minutes to 100 hours without a solvent or in a solvent.

Examples of the solvent include those listed in steps 1 and 2.

Compound (IVa) can be obtained as a commercially available product.

Production Method 2

Compound (I) wherein both of $n^1$ and $n^2$ are 1, and $R^3$ is the formula (A) (compound (Ic)) can be produced by a method given below. Compound (I') wherein both of $n^1$ and $n^2$ are 1, and $R^3$ is the formula (A) can also be similarly produced by the method given below. In addition, compound (I'') wherein both of $n^1$ and $n^2$ are 1, both of $Z^1$ and $Z^2$ are hydrogen atoms, and $R^{3'}$ is the formula (A) can also be similarly produced by the method given below.

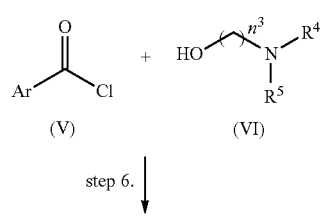

(V)    (VI)

step 6.

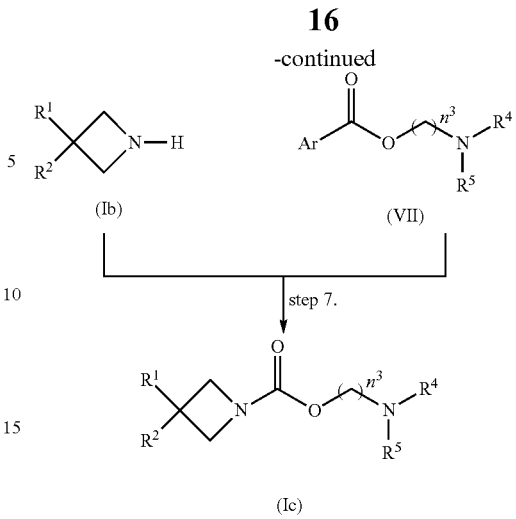

wherein $R^1$, $R^2$, $R^4$, $R^5$, and $n^3$ are each as defined above, and Ar is a substituted phenyl group such as p-nitrophenyl, o-nitrophenyl or p-chlorophenyl, or an unsubstituted phenyl group.

Step 6

Compound (VII) can be produced by reacting compound (V) with compound (VI) at a temperature between −20° C. and 150° C. for 5 minutes to 72 hours, if necessary, preferably in the presence of 1 to 10 equivalents of an additive and/or, if necessary, preferably in the presence of 1 to 10 equivalents of a base, without a solvent or in a solvent.

Examples of the solvent include dichloromethane, chloroform, 1,2-dichloroethane, toluene, ethyl acetate, acetonitrile, diethyl ether, tetrahydrofuran, 1,2-dimethoxyethane, 1,4-dioxane, N,N-dimethylformamide, N,N-dimethylacetamide, N-methylpyrrolidone, dimethyl sulfoxide, or the like. These solvents can be used singly or as a mixture.

Examples of the additive include 1-hydroxybenzotriazole, 4-dimethylaminopyridine, or the like.

Examples of the base include potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), or the like.

Compound (V) can be obtained as a commercially available product.

Compound (VI) can be obtained as a commercially available product or by a known method (e.g., "The Fifth Series of Experimental Chemistry 14, Synthesis of Organic Compound II", 5th edition, p. 1, Maruzen Co., Ltd. (2005)) or a method equivalent thereto.

Step 7

Compound (Ic) can be produced by reacting compound (Ib) with compound (VII) at a temperature between −20° C. and 150° C. for 5 minutes to 72 hours, if necessary in the presence of 1 to 10 equivalents of an additive and/or, if necessary in the presence of 1 to 10 equivalents of a base, without a solvent or in a solvent.

Compound (Ib) can be produced by using ammonia as compound (IVa) in step 5 of Production method 1 or by Production method 7.

Examples of the solvent, the additive and the base include those respectively listed in step 6.

Production Method 3

Compound (I) wherein both of $n^1$ and $n^2$ are 1, and $R^3$ is the formula (B) (compound (Id)) can be produced by a method given below. Compound (I') wherein both of $n^1$ and n² are 1, and R³ is the formula (B) can also be similarly produced by the method given below. In addition, compound (I") wherein both of n¹ and n² are 1, both of $Z^1$ and $Z^2$ are hydrogen atoms, and $R^{3'}$ is the formula (B) can also be similarly produced by the method given below.

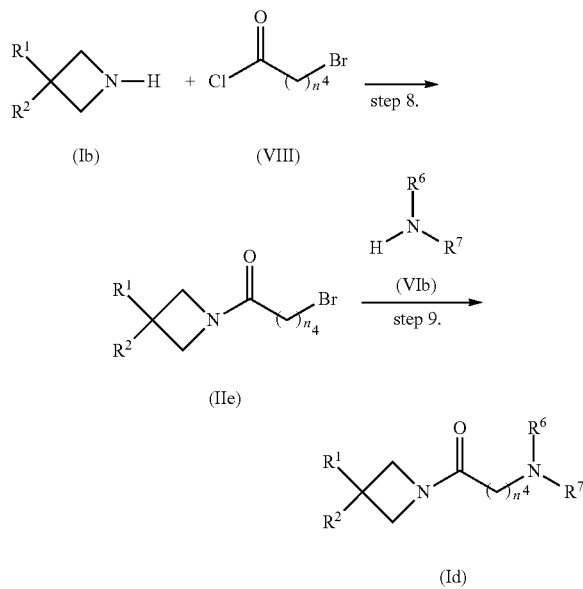

wherein $R^1$, $R^2$, $R^6$, $R^7$, and $n^4$ are each as defined above.

Step 8

Compound (IIe) can be produced by reacting compound (Ib) with compound (VIII) at a temperature between −20° C. and 150° C. for 5 minutes to 72 hours, if necessary, preferably in the presence of 1 to 10 equivalents of a base, without a solvent or in a solvent.

Examples of the solvent include those listed in step 6.

Examples of the base include those listed in step 4.

Compound (VIII) can be obtained as a commercially available product.

Step 9

Compound (Id) can be produced by reacting compound (IIe) with 1 to 20 equivalents of compound (VIb) at a temperature between room temperature and 200° C. for 5 minutes to 100 hours, if necessary in the presence of 1 to 10 equivalents of a base, without a solvent or in a solvent.

Compound (VIb) can be obtained as a commercially available product.

Examples of the solvent include those listed in steps 1 and 2.

Examples of the base include those listed in step 6.

Production Method 4

Compound (IIIa) and compound (IIIb) wherein $R^1$ and/or $R^2$ is C7-C20 alkyloxyC2-C3 alkyl or C7-C20 alkynyloxyC2-C3 alkyl (compound (IIId)) can be produced by a method given below. A compound (which corresponds to compound (IIId)) for use in the production of compound (I') and compound (I") wherein $R^{1'}$ and/or $R^{2'}$ is C7-C20 alkyloxyC2-C3 alkyl, C7-C20 alkenyloxyC2-C3 alkyl, or C7-C20 alkynyloxyC2-C3 alkyl can also be similarly produced by the method given below.

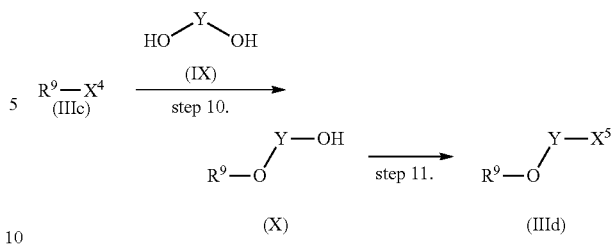

wherein $X^4$ and $X^5$ are as defined in the $X^1$, $R^9$ is alkyl having 7 to 20 carbon atoms as defined in the C7-C20 alkyl moiety in C7-C20 alkyloxyC1-C3 alkyl, alkenyl having 7 to 20 carbon atoms as defined in the C7-C20 alkenyl moiety in C7-C20 alkenyloxyC1-C3 alkyl, or alkynyl having 7 to 20 carbon atoms as defined in the C7-C20 alkynyl moiety in C7-C20 alkynyloxyC1-C3 alkyl, and Y is ethylene or propylene.

Step 10

Compound (X) can be produced by reacting compound (IIIc) with compound (IX) at a temperature between room temperature and 200° C. for 5 minutes to 100 hours, if necessary in the presence of 1 to 10 equivalents of a base, without a solvent or in a solvent.

Examples of the solvent and the base include those respectively listed in step 6.

Compound (IIIc) can be obtained as a commercially available product or by a known method (e.g., "The Fifth Series of Experimental Chemistry 14, Synthesis of Organic Compound II", 5th edition, p. 1, Maruzen Co., Ltd. (2005)) or a method equivalent thereto.

Compound (IX) can be obtained as a commercially available product.

Step 11

Compound (IIId) can be produced by reacting compound (X) with a halogenation reagent or a pseudohalogenation reagent at a temperature between −20° C. and 150° C. for 5 minutes to 100 hours, if necessary, preferably in the presence of 1 to 10 equivalents of a base and if necessary, preferably in the presence of 1 to 10 equivalents of an additive, without a solvent or in a solvent.

Examples of the solvent and the base include those respectively listed in step 6.

Examples of the halogenation reagent or the pseudohalogenation reagent include those listed in step 4.

Examples of the additive include those listed in step 4.

Production Method 5

Compound (I) wherein n¹ is 1, and R³ is alkyl having 1 to 3 carbon atoms (compound (Ie)) can be produced by a method given below. Compound (I') wherein n¹ is 1, and R³ is alkyl having 1 to 3 carbon atoms can also be similarly produced by the method given below. In addition, compound (I") wherein n¹ is 1, both of $Z^1$ and $Z^2$ are hydrogen atoms, and $R^{3'}$ is alkyl having 1 to 3 carbon atoms can also be similarly produced by the method given below.

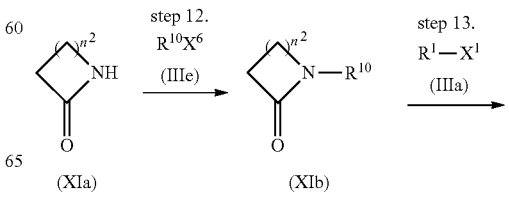

-continued

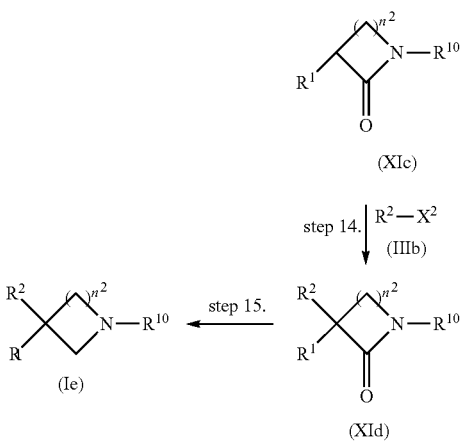

wherein $R^1$, $R^2$, $n^2$, $X^1$, and $X^2$ are each as defined above, $X^6$ is as defined in the $X^1$, and $R^{10}$ is alkyl having 1 to 3 carbon atoms as defined in the alkyl having 1 to 3 carbon atoms represented by $R^3$.

Step 12

Compound (XIb) can be produced by reacting compound (XIa) with compound (IIIe) at a temperature between room temperature and 200° C. for 5 minutes to 100 hours in the presence of 1 to 10 equivalents of a base without a solvent or in a solvent.

Examples of the solvent and the base include those respectively listed in steps 1 and 2.

Compound (XIa) and compound (IIIe) can each be obtained as a commercially available product.

Steps 13 and 14

Compound (XIc) can be produced by reacting compound (XIb) with compound (IIIa) at a temperature between room temperature and 200° C. for 5 minutes to 100 hours in the presence of 1 to 10 equivalents of a base without a solvent or in a solvent. Further, compound (XId) can be produced by reacting compound (XIc) with compound (IIIb) at a temperature between room temperature and 200° C. for 5 minutes to 100 hours in the presence of 1 to 10 equivalents of a base without a solvent or in a solvent.

Examples of the solvent include those listed in step 3.

Examples of the base include lithium diisopropylamide, lithium hexamethyldisilazane, sodium hexamethyldisilazane, n-butyllithium, or the like.

When $R^1$ and $R^2$ are the same, compound (XId) can be obtained by using 2 equivalents or more of compound (IIIa) in step 13.

Step 15

Compound (Ie) can be produced by reacting compound (XId) with 4 to 100 equivalents of a hydride reducing agent at a temperature between −20° C. and 150° C. for 5 minutes to 72 hours, if necessary in the presence of a catalytic amount to 10 equivalents of an additive, in a solvent. In this context, the catalytic amount is as defined above.

Examples of the hydride reducing agent, the additive and the solvent include those listed in step 3.

Production Method 6

Compound (I) wherein $n^1$ and $n^2$ are, the same or different, an integer from 1 to 4 (provided that the case where $n^1$ is 1 and $n^2$ is 1 is excluded), and $R^3$ is a hydrogen atom or alkyl having 1 to 3 carbon atoms (compound (If)) can be produced by a method given below. Compound (I') wherein $n^1$ and $n^2$ are, the same or different, an integer from 1 to 4 (provided that the case where $n^1$ is 1 and $n^2$ is 1 is excluded), and $R^3$ is a hydrogen atom or alkyl having 1 to 3 carbon atoms can also be similarly produced by the method given below. In addition, compound (I″) wherein $n^1$ and $n^2$ are, the same or different, an integer from 1 to 4 (provided that the case where $n^1$ is 1 and $n^2$ is 1 is excluded), both of $Z^1$ and $Z^2$ are hydrogen atoms, and $R^{3'}$ is a hydrogen atom, alkyl having 1 to 3 carbon atoms, hydroxyC2-C4 alkyl, or C1-C3 dialkylamino-C2-C4 alkyl can also be similarly produced by the method given below.

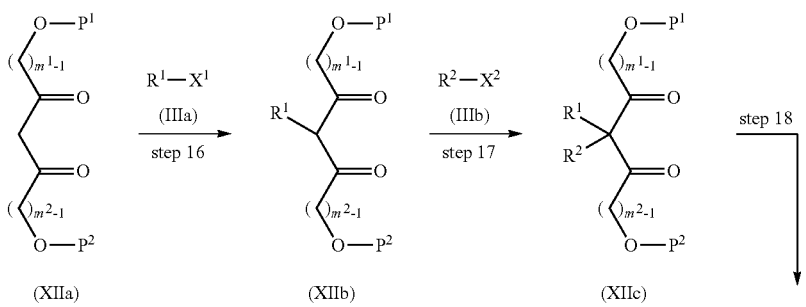

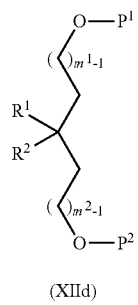

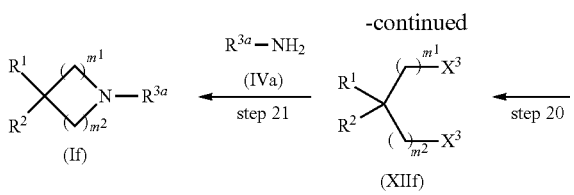
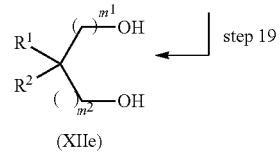

wherein $R^1$, $R^2$, $R^{3a}$, $X^1$, $X^2$, and $X^3$ are each as defined above, $m^1$ and $m^2$ are, the same or different, an integer from 1 to 4 (provided that the case where $m^1$ is 1 and $m^2$ is 1 is excluded), and $P^1$ and $P^2$ are, the same or different, a protective group.

Steps 16 and 17

Compound (XIIb) is obtained in the same way as in step 1 by using compound (XIIa) instead of dimethyl malonate. Compound (XIIc) is obtained in the same way as in step 2 by using compound (XIIb) instead of compound (IIa). When $R^1$ and $R^2$ are the same, compound (XIIc) is obtained by using 2 equivalents or more of compound (IIIa) in step 16. In this context, protective groups commonly used in organic synthetic chemistry [e.g., protective groups described in Protective Groups in Organic Synthesis, third edition, T. W. Greene, John Wiley & Sons Inc. (1999)] can be used as $P^1$ and $P^2$. Compound (XIIa) is obtained by a known method [e.g., "New Experimental Chemistry 14, Synthesis and Reaction of Organic Compound (II)", first edition, p. 751, Maruzen Co., Ltd. (1977) or the like] or a method equivalent thereto.

Step 18

Compound (XIId) is obtained by reducing compound (XIIc) by a known method known [e.g., "New Experimental Chemistry 15, Oxidation and Reduction (II)", first edition, Maruzen Co., Ltd. (1977)] or a method equivalent thereto.

Step 19

Compound (XIIe) is obtained by respectively removing the protective groups $P^1$ and $P^2$ on compound (XIId) by appropriate methods. Methods for removing protective groups commonly used in organic synthetic chemistry [e.g., removal methods described in Protective Groups in Organic Synthesis, third edition, T. W. Greene, John Wiley & Sons Inc. (1999) or the like] can be used as the protective group removal methods. The compound of interest can thereby be produced.

Step 20

Compound (XIIf) is obtained in the same way as in step 4 by using compound (XIIe) instead of compound (IIc).

Step 21

Compound (If) is obtained in the same way as in step 5 by using compound (XIIf) instead of compound (IId).

Production Method 7

Compound (I) wherein each of $n^1$ and $n^2$ is 1, and $R^3$ is a hydrogen atom (compound (Ib)) can be produced by a method given below. Compound (I') wherein each of $n^1$ and $n^2$ is 1, $R^{3'}$ is a hydrogen atom can also be similarly produced by the method given below. In addition, compound (I'') wherein each of $n^1$ and $n^2$ is 1, both of $Z^1$ and $Z^2$ are hydrogen atoms, and $R^{3'}$ is a hydrogen atom can also be similarly produced by the method given below.

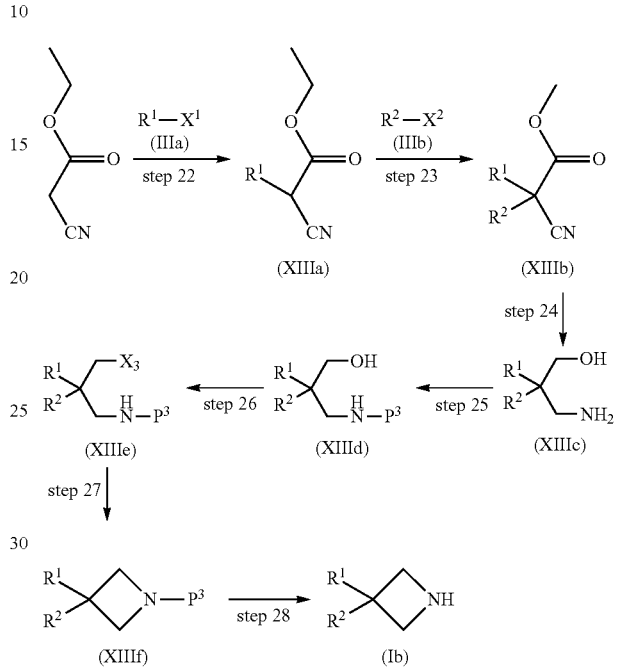

wherein $R^1$, $R^2$, $X^1$, $X^2$, and $X^3$ are each as defined above, and $P^3$ is a protective group such as tert-butoxycarbonyl, o-nitrobenzenesulfonyl or p-methylbenzenesulfonyl.

Steps 22 and 23

Compound (XIIIa) can be produced by reacting ethyl cyanoacetate with compound (IIIa) under the same conditions as in step 1. Further, compound (XIIIb) can be produced by reacting compound (XIIIa) with compound (IIIb) under the same conditions as in step 2.

When $R^1$ and $R^2$ are the same, compound (XIIIb) can be obtained by using 2 equivalents or more of compound (IIIa) in step 22.

Ethyl cyanoacetate can be obtained as a commercially available product.

Compound (IIIa) and compound (IIIb) are the same as those described in Production method 1.

Step 24

Compound (XIIIc) can be produced by reacting compound (XIIIb) under the same conditions as in step 3.

Step 25

Compound (XIIId) can be produced by reacting compound (XIIIc) with 1 to 10 equivalents of di-tert-butoxycarbonyl carbonate, o-nitrobenzenesulfonyl chloride, p-methylbenzenesulfonyl chloride, or the like, at a temperature between 0° C. and 200° C. for 5 minutes to 100 hours in the presence of 1 to 10 equivalents of a base in a solvent.

Examples of the solvent include those listed in step 6.

Examples of the base include those listed in step 4.

Step 26

Compound (XIIIe) can be produced by reacting compound (XIIId) with 1 equivalent or more of a halogenation reagent or a pseudo-halogenation reagent at a temperature between 0° C. and 150° C. for 5 minutes to 100 hours, if necessary, preferably in the presence of 1 to 10 equivalents of a base, without a solvent or in a solvent.

Examples of the halogenation reagent or the pseudohalogenation reagent include those listed in step 4.

Examples of the solvent include those listed in step 3.

Examples of the base include those listed in step 4.

Step 27

Compound (XIIIf) can be produced by intramolecularly reacting compound (XIIIe) at a temperature between 0° C. and 150° C. for 5 minutes to 72 hours if necessary, preferably in the presence of 1 to 10 equivalents of a base, without a solvent or in a solvent.

Examples of the base include potassium carbonate, potassium hydroxide, sodium hydroxide, sodium methoxide, potassium tert-butoxide, triethylamine, diisopropylethylamine, N-methylmorpholine, pyridine, 1,8-diazabicyclo[5.4.0]-7-undecene (DBU), lithium diisopropylamide, lithium hexamethyldisilazane, sodium hexamethyldisilazane, n-butyllithium, or the like.

Examples of the solvent include those listed in steps 1 and 2.

Step 28

Compound (Ib) is obtained by removing the protective group $P^3$ on compound (XIIIf) by an appropriate method. Methods for removing protective groups commonly used in organic synthetic chemistry [e.g., removal methods described in Protective Groups in Organic Synthesis, third edition, T. W. Greene, John Wiley & Sons Inc. (1999) or the like] can be used as the protective group removal method. The compound of interest can thereby be produced.

Production Method 8

Compound (I) wherein each of $n^1$ and $n^2$ is 1, and $R^3$ is alkyl having 1 to 3 carbon atoms (compound (Ig)) can be produced by a method given below. Compound (I') wherein each of $n^1$ and $n^2$ is 1, and $R^3$ is alkyl having 1 to 3 carbon atoms can also be similarly produced by the method given below. In addition, compound (I") wherein each of $n^1$ and $n^2$ is 1, both of $Z^1$ and $Z^2$ are hydrogen atoms, and $R^{3'}$ is alkyl having 1 to 3 carbon atoms can also be similarly produced by the method given below.

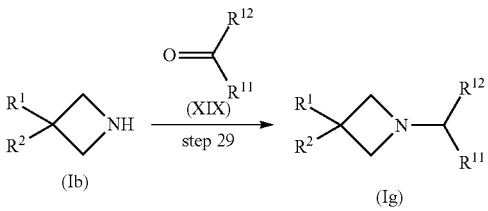

wherein $R^1$ and $R^2$ are each as defined above, $R^{11}$ is a hydrogen atom, methyl or ethyl, and $R^{12}$ is a hydrogen atom or methyl, or $R^{11}$ and $R^{12}$ form a cyclopropyl ring together with the adjacent carbon atom (provided that when $R^{11}$ is a hydrogen atom or ethyl, $R^{12'}$ is not methyl).

Step 29

Compound (Ig) can be produced by reacting compound (Ib), preferably with 1 to 10 equivalents of compound (XIX), at a temperature between −20° C. and 150° C. for 5 minutes to 72 hours in the presence of preferably 1 equivalent to a large excess of a reducing agent and, if necessary, preferably 1 to 10 equivalents of an acid, in a solvent.

Examples of the solvent include methanol, ethanol, dichloromethane, chloroform, 1,2-dichloroethane, toluene, ethyl acetate, acetonitrile, diethyl ether, tetrahydrofuran, 1,2-dimethoxyethane, dioxane, N,N-dimethylformamide, N,N-dimethylacetamide, N-methylpyrrolidone, water, or the like. These solvents are used singly or as a mixture.

Examples of the reducing agent include sodium triacetoxyborohydride, sodium cyanoborohydride, or the like.

Examples of the acid include hydrochloric acid, acetic acid, or the like.

Compound (XIX) can be obtained as a commercially available product.

Production Method 9

Compound (I") wherein each of $n^1$ and $n^2$ is 1, $R^{3'}$ is hydrogen, $Z^1$ is alkyl having 1 to 3 carbon atoms, and $Z^2$ is a hydrogen atom (compound (I"b)) can be produced by a method given below.

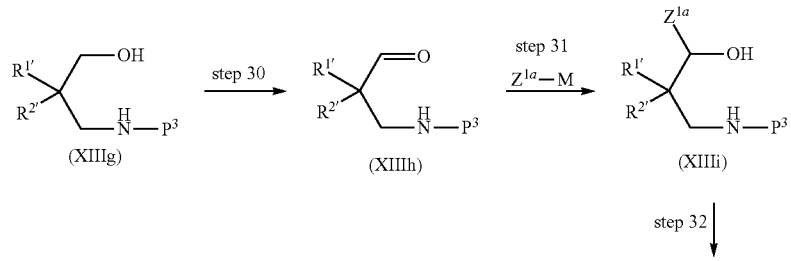

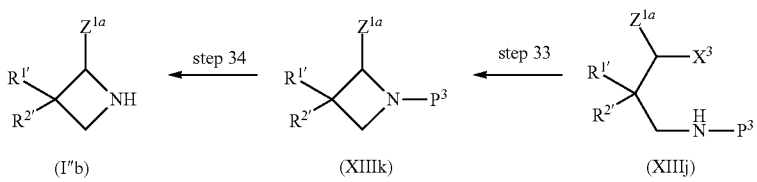

wherein $R^{1'}$, $R^{2'}$, $X^{3'}$ and $P^3$ are each as defined above, $Z^{1a}$ is alkyl having 1 to 3 carbon atoms as defined in the alkyl having 1 to 3 carbon atoms represented by $Z^1$, and M is lithium, magnesium bromide, magnesium chloride, or the like.

Step 30

Compound (XIIIh) can be produced by reacting compound (XIIIg) with 1 to 10 equivalents of an oxidizing agent at a temperature between 0° C. and 150° C. for 5 minutes to 72 hours in a solvent.

Examples of the oxidizing agent include Dess-Martin reagents, pyridinium chlorochromate, pyridinium dichromate, tetrapropylammonium perruthenate, or the like.

Examples of the solvent include those listed in step 6.

Compound (XIIIg) can be produced in the same way as in compound (XIIId) in Production method 7.

Step 31

Compound (XIIIi) can be produced by reacting compound (XIIIh) with 1 to 10 equivalents of an organic metal reagent at a temperature between −78° C. and 100° C. for 5 minutes to 72 hours in a solvent.

Examples of the organic metal reagent include: alkyllithium reagents such as methyllithium and ethyllithium; Grignard reagents such as methyl magnesium bromide and ethyl magnesium bromide; and organic zinc reagents such as dimethyl zinc and diethyl zinc, or the like.

Examples of the solvent include those listed in step 3.

Step 32

Compound (XIIIj) can be produced in the same way as in Step 26.

Step 33

Compound (XIIIk) can be produced in the same way as in Step 27.

Step 34

Compound (I"b) can be produced in the same way as in Step 28.

Production Method 10

Compound (I") wherein each of $n^1$ and $n^2$ is 1, $R^{3'}$ is alkyl having 1 to 3 carbon atoms, $Z^1$ is alkyl having 1 to 3 carbon atoms, and $Z^2$ is a hydrogen atom (compound (I"g)) can be produced by a method given below. Also, compound (I") wherein each of $n^1$ and $n^2$ is 1, $R^{3'}$ is the formula (A), $Z^1$ is alkyl having 1 to 3 carbon atoms, and $Z^2$ is a hydrogen atom (compound (I"c)) can be produced by the method given below. In addition, compound (I") wherein each of $n^1$ and $n^2$ is 1, $R^{3'}$ is the formula (B), $Z^1$ is alkyl having 1 to 3 carbon atoms, and $Z^2$ is a hydrogen atom (compound (I"d)) can be produced by the method given below.

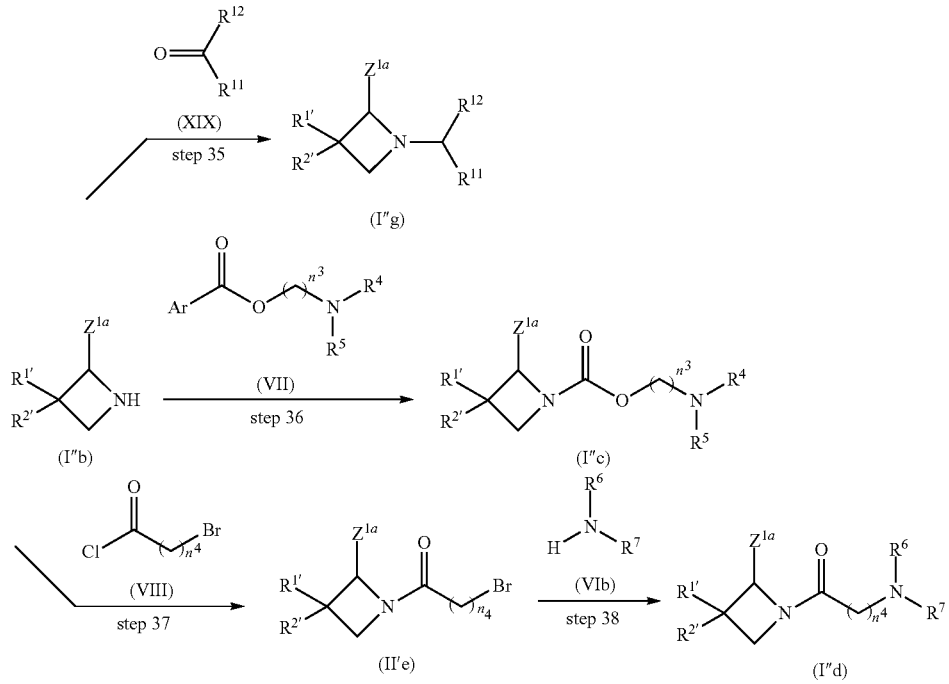

wherein $R^{1'}$, $R^{2'}$, $R^4$, $R^5$, $R^6$, $R^7$, $R^{11}$, $R^{12}$, $n^3$, $n^4$, Ar, and $Z^{1a}$ are each as defined above.

Step 35

Compound (I"g) can be produced in the same way as in Step 29.

Step 36

Compound (I"c) can be produced in the same way as in Step 7.

Step 37

Compound (II'e) can be produced in the same way as in Step 8.

Step 38

Compound (I"d) can be produced in the same way as in Step 9.

Among compounds (I), (I'), and (I"), compounds other than compounds (Ia) to (Ig) and (I"b) to (I"d) described above can be produced according to the production methods described above or by the application of general production methods commonly used in organic synthetic chemistry, by adopting starting materials, reagents, or the like. suitable for the structures of the compounds of interest.

The intermediates and the desired compounds in the production methods described above can each be isolated and purified by separation and purification methods commonly used in organic synthetic chemistry, for example, filtration, extraction, washing, drying, concentration, recrystallization, various chromatography techniques, or the like. Alternatively, each intermediate may be subjected to the next reaction without being particularly purified.

In the cationic lipid of the present invention, hydrogen ions may be coordinated to a lone pair of electrons on the nitrogen atom in the structure, the cationic lipid of the present invention may form a salt with a pharmaceutically acceptable anion, and the cationic lipid of the present invention also encompasses such a compound in which hydrogen ions are coordinated to a lone pair of electrons on the nitrogen atom.

In the present invention, examples of the pharmaceutically acceptable anion include: inorganic ions such as chloride ions, bromide ions, nitrate ions, sulfate ions and phosphate ions; and organic acid ions such as acetate ions, oxalate ions, maleate ions, fumarate ions, citrate ions, benzoate ions, and methanesulfonate ions, or the like.

Some cationic lipids of the present invention may have stereoisomers such as geometric isomers and optical isomers, tautomers, or the like. The cationic lipid of the present invention encompasses all possible isomers including them, and mixtures thereof.

Some or all of the atoms in the cationic lipid of the present invention may be replaced with their corresponding isotopic atoms. Compound (I) also encompasses such a compound containing isotopic atoms replaced therefor. For example, some or all of the hydrogen atoms in compound (I) may each be a hydrogen atom having an atomic weight of 2 (deuterium atom).

The compound derived from the cationic lipid of the present invention by the replacement of some or all of the atoms with their corresponding isotopic atoms can be produced in the same way as in each production method described above by using commercially available building blocks. The compound derived from compound (I) by the replacement of some or all of the hydrogen atoms with deuterium atoms can also be synthesized by use of, for example, a method which involves deuterating an alcohol, a carboxylic acid, or the like using an iridium complex as a catalyst and heavy water as a deuterium source [see J. Am. Chem. Soc., Vol. 124, No. 10, 2092 (2002) or the like].

Concrete examples of the cationic lipid of the present invention are shown in Tables 1 to 3. However, the cationic lipid of the present invention is not intended to be limited to them.

TABLE 1

| Compound No. | Structural formula |
| --- | --- |
| 1 | |
| 2 | |
| 3 | |
| 4 | |
| 5 | |
| 6 | |
| 7 | |

TABLE 2

| Compound No. | Structural formula |
| --- | --- |
| 8 | |

TABLE 2-continued

| Compound No. | Structural formula |
|---|---|
| 9 | (long hydrocarbon chains with double bonds attached to azetidine ring with N-CH2CH2OH) |
| 10 | (long hydrocarbon chains with double bonds attached to azetidine ring with N-CH3) |
| 11 | (long hydrocarbon chains with double bonds attached to azetidine ring with N-CH2CH2CH2-N(CH3)2) |
| 12 | (long hydrocarbon chains with double bonds attached to azetidine ring with N-CH2CH2-N(CH3)2) |
| 13 | (long hydrocarbon chains with double bonds attached to azetidine ring with N-CH3) |
| 14 | (long hydrocarbon chains with double bonds connected via O linkers to azetidine ring with NH) |
| 15 | (long hydrocarbon chains with double bonds connected via O linkers to azetidine ring with N-CH3) |
| 16 | (long hydrocarbon chains with double bonds connected via O linkers to azetidine ring with NH) |
| 17 | (long hydrocarbon chains with double bonds connected via O linkers to azetidine ring with N-CH3) |
| 18 | (long hydrocarbon chains with double bonds attached to methyl-substituted azetidine ring with NH) |
| 19 | (long hydrocarbon chains with double bonds attached to methyl-substituted azetidine ring with N-CH3) |
| 20 | (long hydrocarbon chains with double bonds, one connected via O linker, attached to azetidine ring with N-CH3) |

TABLE 3

| Compound No. | Structural formula |
|---|---|
| 21 | (long hydrocarbon chains with double bonds attached to pyrrolidine ring with N-CH3) |

TABLE 3-continued

| Compound No. | Structural formula |
| --- | --- |
| 22 | |
| 23 | |
| 24 | |
| 25 | |

The nucleic acid used in the present invention can be any molecule as long as the molecule is obtained by the polymerization of, for example, nucleotides and/or molecules having functions equivalent to nucleotides. Examples thereof include ribonucleic acid (RNA) which is a polymer of ribonucleotides, deoxyribonucleic acid (DNA) which is a polymer of deoxyribonucleotides, chimeric nucleic acids consisting of RNA and DNA, and nucleotide polymers derived from these nucleic acids by the replacement of at least one nucleotide with a molecule having a function equivalent to the nucleotide or the like. A derivative at least partially containing the structure of the molecule obtained by the polymerization of nucleotides and/or molecules having functions equivalent to nucleotides is also included in the nucleic acid of the present invention. In the present invention, uracil U and thymine T can be used interchangeably with each other.

Examples of the molecules having functions equivalent to nucleotides include nucleotide derivatives or the like.

The nucleotide derivative can be any molecule as long as the molecule is, for example, a modified nucleotide. For example, a modified ribonucleotide or deoxyribonucleotide molecule is suitably used for improving nuclease resistance or stabilizing the molecule against the other decomposition factors, for enhancing affinity for a complementary strand nucleic acid, for enhancing cell permeability, or for visualizing the molecule, as compared with RNA or DNA.

Examples of the nucleotide derivative include nucleotides modified at the sugar moiety, nucleotides modified at the phosphodiester bond, nucleotides modified at the base, or the like.

The nucleotide modified at the sugar moiety can be, for example, any nucleotide in which a part or the whole of the chemical structure of its sugar is modified or substituted with an arbitrary substituent or substituted with an arbitrary atom. A 2'-modified nucleotide is preferably used.

Examples of the modifying group in the nucleotide modified at the sugar moiety include 2'-cyano, 2'-alkyl, 2'-substituted alkyl, 2'-alkenyl, 2'-substituted alkenyl, 2'-halogen, 2'-O-cyano, 2'-O-alkyl, 2'-O-substituted alkyl, 2'-O-alkenyl, 2'-O-substituted alkenyl, 2'-S-alkyl, 2'-S-substituted alkyl, 2'-S-alkenyl, 2'-S-substituted alkenyl, 2'-amino, 2'-NH-alkyl, 2'-NH-substituted alkyl, 2'-NH-alkenyl, 2'-NH-substituted alkenyl, 2'-SO-alkyl, 2'-SO-substituted alkyl, 2'-carboxy, 2'-CO-alkyl, 2'-CO-substituted alkyl, 2'-Se-alkyl, 2'-Se-substituted alkyl, 2'-SiH$_2$-alkyl, 2'-SiH$_2$-substituted alkyl, 2'-ONO$_2$, 2'-NO$_2$, 2'-N$_3$, 2'-amino acid residues (which results from the removal of a hydroxy group from the carboxylic acids of amino acids), 2'-O-amino acid residues (as defined in the amino acid residues), or the like.

Examples of the nucleotide modified at the sugar moiety include bridged nucleic acid (BNA) having two cyclic structures by the introduction of a bridged structure to the sugar moiety and specifically include locked nucleic acid (LNA) having the oxygen atom at position 2' and the carbon atom at position 4' bridged via methylene ["Tetrahedron Letters", Volume 38, Issue 50, 1997, Pages 8735-8738, and "Tetrahedron", Volume 54, Issue 14, 1998, Pages 3607-3630], ethylene bridged nucleic acid (ENA) ["Nucleic Acid Research", 32, e175 (2004)], or the like.

Further examples of the nucleotide modified at the sugar moiety also include peptide nucleic acid (PNA) [Acc. Chem. Res., 32, 624 (1999)], oxypeptide nucleic acid (OPNA) [J. Am. Chem. Soc., 123, 4653 (2001)], peptide ribonucleic acid (PRNA) [J. Am. Chem. Soc., 122, 6900 (2000)], or the like.

The modifying group in the nucleotide modified at the sugar moiety is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethylaminooxy)ethyl], 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, or the like, further preferably 2'-O-methyl, 2'-O-ethyl, 2'-fluoro, or the like, most preferably 2'-O-methyl and 2'-O-ethyl.

Further, the modifying group in the nucleotide modified at the sugar moiety can also be defined from its size, preferably the modifying group corresponds to a size from fluoro to —O-butyl, and more preferably the modifying group corresponds to a size from —O-methyl to —O-ethyl.

Examples of the alkyl in the modifying group in the nucleotide modified at the sugar moiety include alkyl having 1 to 6 carbon atoms. The alkyl having 1 to 6 carbon atoms is, for example, methyl, ethyl, propyl, isopropyl, butyl, isobutyl, sec-butyl, tert-butyl, pentyl, isopentyl, neopentyl, hexyl or the like.

Examples of the alkenyl in the modifying group in the nucleotide modified at the sugar moiety include alkenyl having 3 to 6 carbon atoms. Examples thereof include allyl, 1-propenyl, butenyl, pentenyl, hexenyl, or the like.

Examples of the halogen in the modifying group in the nucleotide modified at the sugar moiety include a fluorine atom, a chlorine atom, a bromine atom, an iodine atom, or the like.

Examples of the amino acid in the amino acid residue include aliphatic amino acids (specifically, glycine, alanine, valine, leucine, isoleucine, etc.), hydroxyamino acids (specifically, serine, threonine, etc.), acidic amino acids (specifically, aspartic acid, glutamic acid, etc.), acidic amino acid amides (specifically, asparagine, glutamine, etc.), basic amino acids (specifically, lysine, hydroxylysine, arginine, ornithine, etc.), sulfur-containing amino acids (specifically, cysteine, cystine, methionine, etc.), imino acids (specifically, proline, 4-hydroxyproline etc.), or the like.

Examples of the substituent in the substituted alkyl or the substituted alkenyl in the modifying group in the nucleotide modified at the sugar moiety include halogen (as defined above), hydroxy, sulfanyl, amino, oxo, —O-alkyl (the alkyl moiety of the —O-alkyl is as defined in the above-described alkyl having 1 to 6 carbon atoms), —S-alkyl (the alkyl moiety of the —S-alkyl is as defined in the above-described alkyl having 1 to 6 carbon atoms), —NH-alkyl (the alkyl moiety of the —NH-alkyl is as defined in the above-described alkyl having 1 to 6 carbon atoms), dialkylaminooxy (the two alkyl moieties of the dialkylaminooxy are, the same or different, as defined in the above-described alkyl having 1 to 6 carbon atoms), dialkylamino (the two alkyl moieties of the dialkylamino are, the same or different, as defined in the above-described alkyl having 1 to 6 carbon atoms), dialkylaminoalkyloxy (the two alkyl moieties of the dialkylaminoalkyloxy are, the same or different, as defined in the above-described alkyl having 1 to 6 carbon atoms, and the alkylene moiety means a moiety obtained by removal of one hydrogen atom from the alkyl), or the like. The number of substituents is preferably 1 to 3.

The nucleotide modified at the phosphodiester bond can be any nucleotide in which a part or the whole of the chemical structure of its phosphodiester bond is modified or substituted with an arbitrary substituent or substituted with an arbitrary atom. Examples thereof include a nucleotide resulting from the substitution of the phosphodiester bond with a phosphorothioate bond, a nucleotide resulting from the substitution of the phosphodiester bond with a phosphorodithioate bond, a nucleotide resulting from the substitution of the phosphodiester bond with an alkyl phosphonate bond, a nucleotide resulting from the substitution of the phosphodiester bond with a phosphoramidate bond, or the like.

The nucleotide modified at the base can be any nucleotide in which a part or the whole of the chemical structure of its base is modified or substituted with an arbitrary substituent or substituted with an arbitrary atom. Examples thereof include a nucleotide resulting from the substitution of an oxygen atom in the base with a sulfur atom, a nucleotide resulting from the substitution of a hydrogen atom with an alkyl group having 1 to 6 carbon atoms, a nucleotide resulting from the substitution of a methyl group with a hydrogen atom or an alkyl group having 2 to 6 carbon atoms, a nucleotide resulting from the protection of an amino group with a protective group such as an alkyl group having 1 to 6 carbon atoms or an alkanoyl group having 1 to 6 carbon atoms, or the like.

Further examples of the nucleotide derivative include nucleotide derivatives that are modified nucleotides or each have at least one modified sugar moiety, phosphodiester bond or base, and contain an additional chemical substance, such as lipid, phospholipid, phenazine, folate, phenanthridine, anthraquinone, acridine, fluorescein, rhodamine, coumarin, or dye, added thereto, and specifically include 5'-polyamine-added nucleotide derivatives, cholesterol-added nucleotide derivatives, steroid-added nucleotide derivatives, bile acid-added nucleotide derivatives, vitamin-added nucleotide derivatives, green fluorescent dye (Cy3)-added nucleotide derivatives, red fluorescent dye (Cy5)-added nucleotide derivatives, fluorescein (6-FAM)-added nucleotide derivatives, biotin-added nucleotide derivatives, or the like.

In the nucleic acid used in the present invention, the nucleotide or the nucleotide derivative may form a bridged structure, such as an alkylene structure, a peptide structure, a nucleotide structure, an ether structure, an ester structure, and a structure combined with at least one of these structures, with another nucleotide or nucleotide derivative within the nucleic acid.

Examples of the nucleic acid used in the present invention preferably include nucleic acids silencing a target gene and more preferably include nucleic acids having a silencing effect on a target gene through the use of RNA interference (RNAi).

The target gene in the present invention is not particularly limited as long as the gene is expressed by producing mRNA. For example, a gene related to tumor or inflammation is preferred. Examples thereof include genes encoding proteins such as vascular endothelial growth factor (hereinafter, abbreviated to VEGF), vascular endothelial growth factor receptor (hereinafter, abbreviated to VEGFR), fibroblast growth factor, fibroblast growth factor receptor, platelet-derived growth factor, platelet-derived growth factor receptor, hepatocyte growth factor, hepatocyte growth factor receptor, Kruppel-like factor (hereinafter, abbreviated to KLF), expressed sequence tag (Ets) transcription factor, nuclear factor, hypoxia-inducible factor, cell cycle-related factor, chromosomal replication-related factor, chromosomal repair-related factor, microtubule-related factor, growth signal pathway-related factor, growth-related transcription factor, and apoptosis-related factor, or the like, and specifically include VEGF gene, VEGFR gene, fibroblast growth factor gene, fibroblast growth factor receptor gene, platelet-derived growth factor gene, platelet-derived growth factor receptor gene, hepatocyte growth factor gene, hepatocyte growth factor receptor gene, KLF gene, Ets transcription factor gene, nuclear factor gene, hypoxia-inducible factor gene, cell cycle-related factor gene, chromosomal replication-related factor gene, chromosomal repair-related factor gene, microtubule-related factor gene (e.g., CKAP5 gene or the like), growth signal pathway-related factor gene (e.g., KRAS gene or the like), growth-related transcription factor gene, apoptosis-related factor (e.g., BCL-2 gene or the like), or the like.

The target gene according to the present invention is preferably, for example, a gene expressed in the liver, the lung, the kidney, or the spleen, more preferably a gene expressed in the liver. Examples thereof include the aforementioned genes related to tumor or inflammation, and genes encoding proteins such as hepatitis B virus genome, hepatitis C virus genome, apolipoprotein (APO), hydroxymethylglutaryl (HMG) CoA reductase, kexin type 9 serine protease (PCSK9), factor 12, glucagon receptor, glucocorticoid receptor, leukotriene receptor, thromboxane A2 receptor, histamine H1 receptor, carbonic anhydrase, angiotensin-converting enzyme, renin, p53, tyrosine phosphatase (PTP), sodium-dependent glucose transport carrier, tumor necrosis factor, interleukin, hepcidin, trans siren, antithrombin, protein C, and matriptase enzyme (e.g., TMPRSS6 gene or the like), or the like.

Any nucleic acid such as a double-stranded nucleic acid (e.g., siRNA (short interference RNA) and miRNA (micro RNA)) or a single-stranded nucleic acid (e.g., shRNA (short hairpin RNA) antisense nucleic acid and ribozyme) may be used as the nucleic acid silencing a target gene as long as the nucleic acid comprises a nucleotide sequence complementary to, for example, a partial nucleotide sequence of the mRNA of a gene (target gene) encoding a protein or the like and silences the target gene. A double-stranded nucleic acid is preferred.

The nucleic acid comprising a nucleotide sequence complementary to a partial nucleotide sequence of the mRNA of the target gene is referred to as an antisense strand nucleic acid. A nucleic acid comprising a nucleotide sequence complementary to the nucleotide sequence of the antisense strand nucleic acid is also referred to as a sense strand nucleic acid. The sense strand nucleic acid refers to a nucleic acid capable of forming a duplex formation moiety by pairing with the antisense strand nucleic acid, such as a nucleic acid itself consisting of the partial nucleotide sequence of the target gene.

The double-stranded nucleic acid refers to a nucleic acid having a duplex formation moiety composed of paired two strands. The duplex formation moiety refers to a part in which nucleotides constituting the double-stranded nucleic acid, or derivatives thereof have formed a duplex by constituting base pairs. The base pairs constituting the duplex formation moiety are usually 15 to 27 base pairs, preferably 15 to 25 base pairs, more preferably 15 to 23 base pairs, further preferably 15 to 21 base pairs, particularly preferably 15 to 19 base pairs.

For example, a nucleic acid consisting of a partial sequence of the mRNA of the target gene, or a nucleic acid derived from the nucleic acid by the substitution, deletion or addition of 1 to 3 bases, preferably 1 or 2 bases, more preferably 1 base, and having silencing activity against the target protein is suitably used as the antisense strand nucleic acid of the duplex formation moiety. Each single-stranded nucleic acid constituting the double-stranded nucleic acid usually consists of a sequence of 15 to 30 bases (nucleosides), preferably 15 to 29 bases, more preferably 15 to 27 bases, further preferably 15 to 25 bases, particularly preferably 17 to 23 bases, most preferably 19 to 21 bases.

Either of the antisense strand or the sense strand constituting the double-stranded nucleic acid, or both of these nucleic acids may have a non-duplex-forming additional nucleic acid on the 3' or 5' side subsequent to the duplex formation moiety. This non-duplex-forming moiety is also referred to as an overhang.

For example, a double-stranded nucleic acid having an overhang consisting of 1 to 4 bases, usually 1 to 3 bases, at the 3' end or the 5' end of at least one of the strands is used as the double-stranded nucleic acid having the overhang. A double-stranded nucleic acid having an overhang consisting of 2 bases is preferably used, and a double-stranded nucleic acid having an overhang consisting of dTdT or UU is more preferably used. The overhang can be located in only the antisense strand, only the sense strand, and both of the antisense strand and the sense strand. A double-stranded nucleic acid having overhangs in both of the antisense strand and the sense strand is preferably used.

A sequence partially or completely matching the nucleotide sequence of the mRNA of the target gene, or a sequence partially or completely matching the nucleotide sequence of a complementary strand of the mRNA of the target gene may be used subsequently to the duplex formation moiety. Alternatively, for example, a nucleic acid molecule that forms the double-stranded nucleic acid by the action of ribonuclease such as Dicer (International Publication No. WO 2005/089287), a double-stranded nucleic acid having no 3'-terminal or 5'-terminal overhang, or the like can also be used as the nucleic acid silencing the target gene.

When the double-stranded nucleic acid is siRNA, preferably, the antisense strand is an antisense strand in which a sequence of at least the 1st to 17th bases (nucleosides) counted from the 5' end toward the 3' end is a sequence of bases complementary to a sequence of 17 consecutive bases of the mRNA of the target gene. More preferably, the antisense strand is an antisense strand in which a sequence of the 1st to 19th bases counted from the 5' end toward the 3' end is a sequence of bases complementary to a sequence of 19 consecutive bases of the mRNA of the target gene, a sequence of the 1st to 21st bases counted from the 5' end toward the 3' end is a sequence of bases complementary to a sequence of 21 consecutive bases of the mRNA of the target gene, or a sequence of the 1st to 25th bases counted from the 5' end toward the 3' end is a sequence of bases complementary to a sequence of 25 consecutive bases of the mRNA of the target gene.

When the nucleic acid used in the present invention is siRNA, preferably 10 to 70%, more preferably 15 to 60%, further preferably 20 to 50%, of sugars in the nucleic acid is ribose substituted at position 2' with a modifying group. The ribose substituted at position 2' with a modifying group according to the present invention means that the hydroxy group at position 2' of the ribose is substituted with a modifying group. The resulting configuration may be the same as or different from that of the hydroxy group at position 2' of the ribose and is preferably the same as that of the hydroxy group at position 2' of the ribose. Examples of the modifying group in the ribose substituted at position 2' therewith include those listed in the definition of the modifying group in the 2'-modified nucleotide in the nucleotide modified at the sugar moiety, and a hydrogen atom. The modifying group is preferably 2'-cyano, 2'-halogen, 2'-O-cyano, 2'-alkyl, 2'-substituted alkyl, 2'-O-alkyl, 2'-O-substituted alkyl, 2'-O-alkenyl, 2'-O-substituted alkenyl, 2'-Se-alkyl, 2'-Se-substituted alkyl, or the like, more preferably 2'-cyano, 2'-fluoro, 2'-chloro, 2'-bromo, 2'-trifluoromethyl, 2'-O-methyl, 2'-O-ethyl, 2'-O-isopropyl, 2'-O-trifluoromethyl, 2'-O-[2-(methoxy)ethyl], 2'-O-(3-aminopropyl), 2'-O-[2-(N,N-dimethyl)aminooxy]ethyl, 2'-O-[3-(N,N-dimethylamino)propyl], 2'-O-{2-[2-(N,N-dimethylamino)ethoxy]ethyl}, 2'-O-[2-(methylamino)-2-oxoethyl], 2'-Se-methyl, a hydrogen atom, or the like, further preferably 2'-O-methyl, 2'-O-ethyl, 2'-fluoro, a hydrogen atom, or the like, most preferably 2'-O-methyl and 2'-O-fluoro.

The nucleic acid used in the present invention encompasses derivatives in which, for example, an oxygen atom contained in a phosphoric acid moiety, an ester moiety, or the like in the structure of the nucleic acid, or the like is substituted with a different atom such as a sulfur atom.

The hydroxy group at position 5' of a sugar attached to the 5' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The hydroxy group at position 3' of a sugar attached to the 3' terminal base of the antisense strand or the sense strand may be modified with a phosphoric acid group or any of the aforementioned modifying groups, or with a group that is converted to a phosphoric acid group or any of the aforementioned modifying groups by an in vivo nucleolytic enzyme or the like.

The single-stranded nucleic acid can be, for example, any nucleic acid consisting of a sequence complementary to a sequence consisting of 15 to 27 consecutive bases (nucleosides), preferably 15 to 25 consecutive bases, more preferably 15 to 23 consecutive bases, further preferably 15 to 21 consecutive bases, particularly preferably 15 to 19 consecutive bases, of the target gene, or any nucleic acid derived from the nucleic acid by the substitution, deletion or addition of 1 to 3 bases, preferably 1 or 2 bases, more preferably 1 base, and having silencing activity against the target protein. The single-stranded nucleic acid preferably consists of a sequence of 15 to 30 bases (nucleosides). More preferably, a single-stranded nucleic acid of 15 to 27 bases, further preferably 15 to 25 bases, particularly preferably 15 to 23 bases, is suitably used.

A linkage via a spacer sequence (spacer oligonucleotide) of the antisense strand and the sense strand constituting the double-stranded nucleic acid described above may be used as the single-stranded nucleic acid. The spacer oligonucleotide is preferably a single-stranded nucleic acid molecule of 6 to 12 bases. Its 5'-terminal sequence is preferably UU. Examples of the spacer oligonucleotide include a nucleic acid consisting of a sequence UUCAAGAGA. The order in which the antisense strand and the sense strand are linked via the spacer oligonucleotide can be any order in which either of the strands may be positioned on the 5' side. The single-stranded nucleic acid is preferably a single-stranded nucleic acid such as shRNA having a duplex formation moiety by, for example, a stem-loop structure. The single-stranded nucleic acid such as shRNA is usually 50 to 70 bases long.

A nucleic acid of 70 bases or smaller in length, preferably 50 bases or smaller in length, more preferably 30 bases or smaller in length, designed to form the single-stranded nucleic acid or the double-stranded nucleic acid by the action of ribonuclease or the like may be used.

The nucleic acid used in the present invention can be produced by use of a known RNA or DNA synthesis method and RNA or DNA modification method.

The composition of the present invention is a composition containing the cationic lipid of the present invention and a nucleic acid. Examples thereof include a composition containing a complex of the cationic lipid of the present invention and the nucleic acid, or a complex of the cationic lipid of the present invention combined with a neutral lipid and/or a polymer and the nucleic acid, a composition containing the complex and a lipid membrane with which the complex is enclosed, or the like. The lipid membrane may be a lipid monolayer (lipid monomolecular membrane) or a lipid bilayer (lipid bimolecular membrane). The cationic lipid of the present invention, a neutral lipid and/or a polymer may be contained in the lipid membrane. Also, a cationic lipid other than the cationic lipid of the present invention may be contained in the complex and/or the lipid membrane.

Other examples of the composition of the present invention also include a composition containing a complex of a cationic lipid other than the cationic lipid of the present invention and the nucleic acid, or a complex of a cationic lipid other than the cationic lipid of the present invention combined with a neutral lipid and/or a polymer and the nucleic acid, and a lipid membrane with which the complex is enclosed, wherein the cationic lipid of the present invention is contained in the lipid membrane, or the like. In this case as well, the lipid membrane may be a lipid monolayer (lipid monomolecular membrane) or a lipid bilayer (lipid bimolecular membrane). A cationic lipid other than the cationic lipid of the present invention, a neutral lipid and/or a polymer may be contained in the lipid membrane.

The composition of the present invention is more preferably a composition containing a complex of the cationic lipid of the present invention and the nucleic acid, a composition containing a complex of the cationic lipid of the present invention and the nucleic acid, and a lipid membrane with which the complex is enclosed, wherein the cationic lipid of the present invention is contained in the lipid membrane, and a composition containing a complex of a cationic lipid other than the cationic lipid of the present invention and the nucleic acid, and a lipid membrane with which the complex is enclosed, wherein the cationic lipid of the present invention is contained in the lipid membrane, further preferably a composition containing a complex of the cationic lipid of the present invention and the nucleic acid, and a composition containing a complex of the cationic lipid of the present invention and the nucleic acid, and a lipid membrane with which the complex is enclosed, wherein the cationic lipid of the present invention is contained in the lipid membrane, most preferably a composition containing a complex of the cationic lipid of the present invention and the nucleic acid, and a lipid membrane with which the complex is enclosed, wherein the cationic lipid of the present invention is contained in the lipid membrane. In any of the cases, a neutral lipid and/or a polymer may be contained in the lipid membrane. Also, a cationic lipid other than the cationic lipid of the present invention may be contained in the complex and/or the lipid membrane.

Examples of the form of the complex include a complex of the nucleic acid and a membrane (inverse micelle) consisting of a lipid monolayer (monomolecular layer), a complex of the nucleic acid and a liposome, and a complex of the nucleic acid and a micelle, or the like, and preferably include a complex of the nucleic acid and a membrane consisting of a lipid monolayer, and a complex of the nucleic acid and a liposome.

Examples of the composition containing the complex and a lipid membrane with which the complex is enclosed include a liposome containing the complex and a lipid bilayer with which the complex is enclosed, or the like.

One or more cationic lipids of the present invention may be used in the composition of the present invention. Also, the cationic lipid of the present invention may be mixed with a cationic lipid other than the cationic lipid of the present invention.

Examples of the cationic lipid other than the cationic lipid of the present invention include: N-[1-(2,3-dioleyloxy)propyl]-N,N,N-trimethylammonium chloride (DOTMA), N-(2,3-di-(9-(Z)-octadecenoyloxy))-prop-1-yl-N,N,N-trimethyl-ammonium chloride (DOTAP), or the like, disclosed in Japanese Patent Laid-Open No. 61-161246 (U.S. Pat. No.

5,049,386); N-[1-(2,3-dioleyloxypropyl)]-N,N-dimethyl-N-hydroxyethyl ammonium bromide (DORIE), 2,3-dioleyloxy-N-[2-(sperminecarboxamide)ethyl]-N,N-dimethyl-1-propanaminium trifluoroacetic acid (DOSPA), or the like, disclosed in International Publication Nos. WO 91/16024 and WO 97/019675; DLinDMA or the like, disclosed in International Publication No. WO 2005/121348; DLin-K-DMA disclosed in International Publication No. WO 2009/086558; and (3R,4R)-3,4-bis((Z)-hexadec-9-enyloxy)-1-methylpyrrolidine, N-methyl-N,N-bis(2-((Z)-octadec-6-enyloxy)ethyl)amine, or the like, disclosed in International Publication No. WO 2011/136368. Examples thereof preferably include cationic lipids having a tertiary amine site having two unsubstituted alkyl groups or a quaternary ammonium site having three unsubstituted alkyl groups, such as DOTMA, DOTAP, DORIE, DOSPA, 1,2-dilinoleyloxy-N,N-dimethylaminopropane (DLinDMA), and 2,2-dilinoleyl-4-dimethylaminomethyl-[1,3]-dioxolane (DLin-K-DMA), and more preferably include cationic lipids having the tertiary amine site. The unsubstituted alkyl groups in the tertiary amine site or the quaternary ammonium site are more preferably methyl groups.

The composition of the present invention can contain the nucleic acid and can also contain a compound chemically analogous to the nucleic acid.

The composition of the present invention can be produced according to a production method known in the art or a method equivalent thereto and may be produced by any production method. For example, a liposome preparation method known in the art can be applied to the production of a composition containing a liposome, which is a composition. Examples of the liposome preparation method known in the art include a liposome preparation method of Bangham et al. [see "J. Mol. Biol.", 1965, Vol. 13, p. 238-252], an ethanol injection method [see "J. Cell Biol.", 1975, Vol. 66, p. 621-634], a French press method [see "FEBS Lett.", 1979, Vol. 99, p. 210-214], a freezing-thawing method [see "Arch. Biochem. Biophys.", 1981, Vol. 212, p. 186-194], a reverse-phase evaporation method [see "Proc. Natl. Acad. Sci. USA", 1978, Vol. 75, p. 4194-4198], a pH gradient method (see e.g., Japanese Patent Nos. 2572554 and 2659136 or the like), or the like. For example, water, an acid, an alkali, various buffer solutions, physiological saline, an amino acid transfusion of the like can be used as a solution for dispersing the liposome in the production of the liposome. In the production of the liposome, for example, an antioxidant such as citric acid, ascorbic acid, cysteine, or ethylenediaminetetraacetic acid (EDTA); or a tonicity agent such as glycerin, glucose, or sodium chloride, or the like may also be added. Alternatively, the liposome can also be produced, for example, by dissolving the cationic lipid of the present invention, a mixture of the cationic lipid of the present invention and a cationic lipid other than the cationic lipid of the present invention, or the like, for example, in an organic solvent such as ethanol, distilling off the solvent, then adding physiological saline or the like to the residue, and shaking and stirring the mixture to form the liposome.

Also, the composition of the present invention can be produced by, for example, a production method which involves dissolving the cationic lipid of the present invention, or a mixture of the cationic lipid of the present invention and a cationic lipid other than the cationic lipid of the present invention in chloroform in advance, subsequently adding an aqueous solution of the nucleic acid and methanol to the solution, mixing the mixture to form a cationic lipid/nucleic acid complex, further isolating the chloroform layer, and adding thereto polyethylene glycolated phospholipid, a neutral lipid and water to form a water-in-oil (W/O) emulsion, which is then treated by the reverse-phase evaporation method (see National Publication of International Patent Application No. 2002-508765), or a production method which involves dissolving the nucleic acid in an aqueous solution of an acidic electrolyte, adding, for example, a mixture of the cationic lipid of the present invention, or a mixture of the cationic lipid of the present invention and a cationic lipid other than the cationic lipid of the present invention (in ethanol) to the solution, decreasing the ethanol concentration to 20 v/v % to prepare a liposome containing the nucleic acid, removing excessive ethanol by dialysis after sizing and filtration, and then dialyzing the sample by further elevating pH to remove the nucleic acid attached to the surface of the composition (see National Publication of International Patent Application No. 2002-501511 and Biochimica et Biophysica Acta, 2001, Vol. 1510, p. 152-166), or the like.

Among the compositions of the present invention, a composition containing a liposome containing a complex of the cationic lipid of the present invention and the nucleic acid, or a complex of the cationic lipid of the present invention combined with a neutral lipid and/or a polymer and the nucleic acid, and a lipid bilayer with which the complex is enclosed can be produced according to production methods described in, for example, International Publication Nos. WO 02/28367 and WO 2006/080118 or the like.

Among the compositions of the present invention, for example, a composition containing a complex of the cationic lipid of the present invention and the nucleic acid, or a complex of the cationic lipid of the present invention combined with a neutral lipid and/or a polymer and the nucleic acid, and a lipid membrane with which the complex is enclosed, a composition containing a complex of a cationic lipid other than the cationic lipid of the present invention and the nucleic acid, or a complex of a cationic lipid other than the cationic lipid of the present invention combined with a neutral lipid and/or a polymer and the nucleic acid, and a lipid membrane with which the complex is enclosed, wherein the cationic lipid of the present invention is contained in the lipid membrane, or the like can be obtained according to production methods described in, for example, International Publication Nos. WO 02/28367 and WO 2006/080118 or the like, by producing each complex, dispersing the complex in water or a 0 to 40% aqueous ethanol solution without dissolution (liquid A), aside from this, dissolving each lipid membrane component in, for example, an aqueous ethanol solution (liquid B), mixing the liquid A and the liquid B in equal amounts or at a volume ratio of 1:1 to 7:3, and further appropriately adding water thereto. One or more cationic lipids of the present invention or cationic lipids other than the cationic lipid of the present invention can be used as cationic lipids in the liquids A and B. Alternatively, the cationic lipid of the present invention and the cationic lipid other than the cationic lipid of the present invention may be combined and used as a mixture.

In the present invention, during and after production of, for example, the composition containing a complex of the cationic lipid of the present invention and the nucleic acid, or a complex of the cationic lipid of the present invention combined with a neutral lipid and/or a polymer and the nucleic acid, and a lipid membrane with which the complex is enclosed, the composition containing a complex of a cationic lipid other than the cationic lipid of the present invention and the nucleic acid, or a complex of a cationic lipid other than the cationic lipid of the present invention combined with a neutral lipid and/or a polymer and the nucleic acid, and a lipid membrane with which the complex is enclosed, wherein the cationic lipid of the present invention is contained in the lipid membrane, or the like, the structures of the complex and the membrane may be varied due to the electrostatic interaction between the nucleic acid in the complex and the cationic lipid in the lipid membrane, or the fusion of the cationic lipid in the complex with the cationic lipid in the lipid membrane. Such a composition is also included in, for example, the composition containing a complex of the cationic lipid of the present invention and the nucleic acid, or a complex of the cationic lipid of the present invention combined with a neutral lipid and/or a polymer and the nucleic acid, and a lipid membrane with which the complex is enclosed, the composition containing a complex of a cationic lipid other than the cationic lipid of the present invention and the nucleic acid, or a complex of a cationic lipid other than the cationic lipid of the present invention combined with a neutral lipid and/or a polymer and the nucleic acid, and a lipid membrane with which the complex is enclosed, wherein the cationic lipid of the present invention is contained in the lipid membrane, or the like.

The composition containing the nucleic acid and the cationic lipid can also be obtained according to production methods described in, for example, International Publication Nos. WO 02/28367 and WO 2006/080118, or the like, by producing a complex of the nucleic acid (as defined above), preferably the double-stranded nucleic acid, and a liposome containing the cationic lipid of the present invention and/or a cationic lipid other than the cationic lipid of the present invention, dispersing the complex in water or a 0 to 40% aqueous ethanol solution without dissolution (liquid A), aside from this, dissolving the cationic lipid of the present invention and/or a cationic lipid other than the cationic lipid of the present invention in an aqueous ethanol solution (liquid B), mixing the liquid A and the liquid B in equal amounts or at a volume ratio of 1:1 to 7:3, and further appropriately adding water thereto. This composition is preferably a composition containing a complex of the cationic lipid and the nucleic acid, and a lipid membrane with which the complex is enclosed, or a composition containing a complex of the nucleic acid and a membrane (inverse micelle) consisting of a lipid monolayer containing the cationic lipid, and a lipid membrane with which the complex is enclosed. In these cases, the lipid membrane may be a lipid monolayer (lipid monomolecular membrane) or a lipid bilayer (lipid bimolecular membrane).

The liposome in the complex of the nucleic acid and the liposome as disclosed herein is preferably a liposome size-adjusted in advance to an average particle size of 10 nm to 400 nm, more preferably 20 nm to 110 nm, further preferably 30 nm to 80 nm. A neutral lipid and/or a polymer may be contained in the complex and/or the lipid membrane. The liquid A may have an ethanol concentration of 20 to 70% as long as the complex of the liposome and the nucleic acid can be formed.

Instead of mixing the liquid A and the liquid B in equal amounts, the liquid A and the liquid B may be mixed at a ratio that does not dissolve the complex after the mixing and adjusts an ethanol concentration so as not to dissolve the cationic lipid in the liquid B. Preferably, the liquid A and the liquid B may instead be mixed at a ratio that neither dissolves the complex nor the cationic lipid in the liquid B and creates an aqueous ethanol solution having an ethanol concentration of 30 to 60%. Alternatively, the liquid A and the liquid B may be mixed at a ratio that adjusts an ethanol concentration so as not to dissolve the complex after the mixing of the liquid A and the liquid B, and the ethanol concentration is further adjusted by the addition of water so as not to dissolve the cationic lipid in the liquid B.

The complex of the nucleic acid and the liposome in the liquid A as disclosed herein is morphologically converted to a complex of a membrane (inverse micelle) consisting of a lipid monolayer containing the cationic lipid and the nucleic acid after the mixing of the liquid A and the liquid B and the further appropriate addition of water. The composition containing the nucleic acid and the cationic lipid obtained by the production method as disclosed herein is preferably a composition containing a complex of the cationic lipid and the nucleic acid, and a lipid membrane with which the complex is enclosed, or a composition containing a complex of a membrane (inverse micelle) consisting of a lipid monolayer containing the cationic lipid and the nucleic acid, and a lipid membrane with which the complex is enclosed, wherein the cationic lipid is contained in the lipid membrane. Such a composition is excellent in productivity (yield and/or homogeneity).

In the composition of the present invention, the total number of molecules of the cationic lipid of the present invention in the complex is preferably 0.5 to 4 times, more preferably 1.5 to 3.5 times, further preferably 2 to 3 times the number of phosphorus atoms of the nucleic acid. The total number of molecules of the cationic lipid of the present invention and the cationic lipid other than the cationic lipid of the present invention in the complex is preferably 0.5 to 4 times, more preferably 1.5 to 3.5 times, further preferably 2 to 3 times the number of phosphorus atoms of the nucleic acid.

In the composition of the present invention, the total number of molecules of the cationic lipid of the present invention in the composition containing the complex and a lipid membrane with which the complex is enclosed is preferably 1 to 10 times, more preferably 2.5 to 9 times, further preferably 3.5 to 8 times the number of phosphorus atoms of the nucleic acid. The total number of molecules of the cationic lipid of the present invention and the cationic lipid other than the cationic lipid of the present invention in this composition is preferably 1 to 10 times, more preferably 2.5 to 9 times, further preferably 3.5 to 8 times the number of phosphorus atoms of the nucleic acid.

The neutral lipid can be any of simple lipids, complex lipids, and derived lipids. Examples thereof include, but are not limited to phospholipids, glyceroglycolipids, sphingoglycolipids, sphingoid, sterol, or the like.

When the composition of the present invention contains a neutral lipid, the total number of molecules of the neutral lipid is preferably 0.1 to 2 times, more preferably 0.2 to 1.5 times, further preferably 0.3 to 1.2 times the total number of molecules of the cationic lipid of the present invention and the cationic lipid other than the cationic lipid of the present invention. In any composition of the present invention, the neutral lipid may be contained in the complex or may be contained in the lipid membrane with which the complex is enclosed. More preferably, the neutral lipid is contained at least in the lipid membrane with which the complex is enclosed. Further preferably, the neutral lipid is contained in both of the complex and the lipid membrane with which the complex is enclosed.

Examples of the phospholipid as the neutral lipid include natural or synthetic phospholipids such as phosphatidylcholines (specifically, soybean phosphatidylcholine, egg phosphatidylcholine (EPC), distearoyl phosphatidylcholine (DSPC), dipalmitoyl phosphatidylcholine (DPPC), palmitoyl oleoyl phosphatidylcholine (POPC), dimyristoyl phosphatidylcholine (DMPC), dioleoyl phosphatidylcholine (DOPC), etc.), phosphatidylethanolamines (specifically distearoyl phosphatidylethanolamine (DSPE), dipalmitoyl phosphatidylethanolamine (DPPE), dioleoyl phosphatidylethanolamine (DOPE), dimyristoyl phosphatidylethanolamine (DMPE), 16-O-monomethyl PE, 16-0-dimethyl PE, 18-1-trans PE, palmitoyl oleoyl-phosphatidylethanolamine (POPE), 1-stearoyl-2-oleoyl-phosphatidylethanolamine (SOPE), etc.), glycerophospholipids (specifically, phosphatidylserine, phosphatidic acid, phosphatidylglycerol, phosphatidylinositol, palmitoyl oleoyl phosphatidylglycerol (POPG), lysophosphatidylcholine, etc.), sphingophospholipids (specifically, sphingomyelin, ceramide phosphoethanolamine, ceramide phosphoglycerol, ceramide phosphoglycerophosphoric acid, etc.), glycerophosphonolipids, sphingophosphonolipids, natural lecithins (specifically, egg lecithin, soybean lecithin, etc.), hydrogenated phospholipids (specifically, hydrogenated soybean phosphatidylcholine, etc.), or the like.

Examples of the glyceroglycolipid as the neutral lipid include sulfoxyribosyl glyceride, diglycosyl diglyceride, digalactosyl diglyceride, galactosyl diglyceride, glycosyl diglyceride, or the like.

Examples of the sphingoglycolipid as the neutral lipid include galactosyl cerebroside, lactosyl cerebroside, ganglioside, or the like.

Examples of the sphingoid as the neutral lipid include sphingan, icosasphingan, sphingosine, and derivatives of the foregoing, or the like. Examples of the derivatives include substances derived from sphingan, icosasphingan, sphingosine, or the like by the conversion of —NH$_2$ to —NHCO (CH$_2$)$_x$CH$_3$ wherein x is an integer from 0 to 18 and is particularly preferably 6, 12, or 18).

Examples of the sterol as the neutral lipid include cholesterol, dihydrocholesterol, lanosterol, β-sitosterol, campesterol, stigmasterol, brassicasterol, erugosterol, fucosterol, 3β-[N—(N',N'-dimethylaminoethyl)carbamoyl]cholesterol (DC-Chol), or the like.

Examples of the polymer include polymers such as proteins, albumin, dextran, Polyfect, chitosan, dextran sulfate, poly-L-lysine, polyethylenimine, polyaspartic acid, styrene-maleic acid copolymers, isopropylacrylamide-acrylpyrrolidone copolymers, polyethylene glycol-modified dendrimers, polylactic acid, polylactic acid-polyglycolic acid, and polyethylene glycolated polylactic acid, micelles consisting of one or more of salts of the foregoing, or the like.

In this context, the salt of the polymer encompasses metal salts, ammonium salts, acid-addition salts, organic amine-addition salts, amino acid-addition salts, or the like. Examples of the metal salts include: alkali metal salts such as lithium salt, sodium salt, and potassium salt; alkaline earth metal salts such as magnesium salt and calcium salt; aluminum salts; and zinc salts, or the like. Examples of the ammonium salts include salts of ammonium, tetramethylammonium, or the like. Examples of the acid-addition salts include: inorganic acid salts such as hydrochloride, sulfate, nitrate, and phosphate; and organic acid salts such as acetate, maleate, fumarate, and citrate. Examples of the organic amine-addition salts include addition salts of morpholine, piperidine, or the like. Examples of the amino acid-addition salts include addition salts of glycine, phenylalanine, aspartic acid, glutamic acid, lysine, or the like.

Also, any composition of the present invention preferably contains a lipid derivative or a fatty acid derivative of one or more substances selected from, for example, sugars, peptides, nucleic acids and water-soluble polymers, a surfactant, or the like. The derivative, the surfactant or the like may be contained in the complex or may be contained in the lipid membrane with which the complex is enclosed, and is more preferably contained in both of the complex and the lipid membrane with which the complex is enclosed.

When the composition of the present invention contains a lipid derivative or a fatty acid derivative of one or more substances selected from sugars, peptides, nucleic acids, and water-soluble polymers, the total number of molecules of the lipid derivative or the fatty acid derivative of one or more substances selected from sugars, peptides, nucleic acids, and water-soluble polymers is preferably 0.01 to 0.3 times, more preferably 0.02 to 0.25 times, further preferably 0.03 to 0.15 times the total number of molecules of the cationic lipid of the present invention and the cationic lipid other than the cationic lipid of the present invention.

Examples of the lipid derivative or the fatty acid derivative of one or more substances selected from sugars, peptides, nucleic acids, and water-soluble polymers, or the surfactant preferably include glycolipids, and lipid derivatives or fatty acid derivatives of water-soluble polymers and more preferably include lipid derivatives or fatty acid derivatives of water-soluble polymers. The lipid derivative or the fatty acid derivative of one or more substances selected from sugars, peptides, nucleic acids, and water-soluble polymers, or the surfactant is preferably a two-faced substance in which a part of the molecule has the properties of binding to other constituents of the composition via, for example, hydrophobic affinity, electrostatic interaction, or the like and the other moiety has the properties of binding to a solvent for use in the production of the composition via, for example, hydrophilic affinity, electrostatic interaction, or the like.

Examples of the lipid derivatives or the fatty acid derivatives of sugars, peptides or nucleic acids include substances obtained by the binding of sugars such as sucrose, sorbitol, and lactose, peptides such as casein-derived peptides, ovalbumin-derived peptides, soybean-derived peptides, and glutathione, or nucleic acids such as DNA, RNA, plasmids, siRNA, and ODN to the neutral lipids or the cationic lipids of the present invention listed in the definition of the composition or to fatty acids such as stearic acid, palmitic acid, myristic acid, and lauric acid, or the like.

Examples of the lipid derivatives or the fatty acid derivatives of sugars also include the glyceroglycolipids or the sphingoglycolipids listed in the definition of the composition, or the like.

Examples of the lipid derivatives or the fatty acid derivatives of water-soluble polymers include substances obtained by the binding of polyethylene glycol, polyglycerin, polyethylenimine, polyvinyl alcohol, polyacrylic acid, polyacrylamide, oligosaccharide, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like or derivatives of the foregoing to the neutral lipids or the cationic lipids of the present invention listed in the definition of the composition or to fatty acids such as stearic acid, palmitic acid, myristic acid, and lauric acid, salts of the foregoing. Examples thereof more preferably include lipid derivatives or fatty acid derivatives of polyethylene glycol or polyglycerin, and salts of the foregoing and further preferably include lipid derivatives or fatty acid derivatives of polyethylene glycol and salts of the foregoing.

Examples of the lipid derivatives or the fatty acid derivatives of polyethylene glycol include polyethylene glycolated lipids [specifically, polyethylene glycol-phosphatidylethanolamine (more specifically, 1,2-distearoyl-sn-glycero-3- phosphoethanolamine-N-[methoxy(polyethylene glycol)-2000] (PEG-DSPE), 1,2-dimyristoyl-sn-glycero-3-phosphoethanolamine-N-[methoxy(polyethylene glycol)-2000] (PEG-DMPE), etc.), polyoxyethylene hydrogenated castor oil 60, CREMOPHOR EL, etc.], polyethylene glycol sorbitan fatty acid esters (specifically, polyoxyethylene sorbitan monooleate, etc.), or the like, and polyethylene glycol fatty acid esters and more preferably include polyethylene glycolated lipids.

Examples of the lipid derivatives or the fatty acid derivatives of polyglycerin include polyglycerinated lipids (specifically, polyglycerin-phosphatidylethanolamine, etc.), polyglycerin fatty acid esters, or the like and more preferably include polyglycerinated lipids.

Examples of the surfactant include polyoxyethylene sorbitan monooleate (specifically, polysorbate 80, etc.), polyoxyethylene polyoxypropylene glycol (specifically, Pluronic F68, etc.), sorbitan fatty acid esters (specifically, sorbitan monolaurate, sorbitan monooleate, etc.), polyoxyethylene derivatives (specifically, polyoxyethylene hydrogenated castor oil 60, polyoxyethylene lauryl alcohol, etc.), glycerin fatty acid esters, polyethylene glycol alkyl ethers, or the like and preferably include polyoxyethylene polyoxypropylene glycol, glycerin fatty acid esters and polyethylene glycol alkyl ethers.

The complex and the lipid membrane in the composition of the present invention can each be arbitrarily surface-modified with, for example, a water-soluble polymer or the like[see D. D. Lasic and F. Martin ed., "Stealth Liposomes" (USA), CRC Press Inc.), 1995, p. 93-102]. Examples of the water-soluble polymer that may be used in the surface modification include polyethylene glycol, polyglycerin, polyethylenimine, polyvinyl alcohol, polyacrylic acid, polyacrylamide, oligosaccharides, dextrin, water-soluble cellulose, dextran, chondroitin sulfate, polyglycerin, chitosan, polyvinylpyrrolidone, polyaspartic acid amide, poly-L-lysine, mannan, pullulan, oligoglycerol, or the like and preferably include dextran, pullulan, mannan, amylopectin, hydroxyethyl starch, or the like. The lipid derivative, the fatty acid derivative of one or more substances selected from sugars, peptides, nucleic acids, and water-soluble polymers (as defined above), or the like can also be used in the surface modification. The surface modification is a method for allowing the complex and the lipid membrane in the composition of the present invention to contain the lipid derivative or the fatty acid derivative of one or more substances selected from sugars, peptides, nucleic acids, and water-soluble polymers, or the surfactant.

A targeting ligand can be arbitrarily bonded directly to the surface of the composition of the present invention through a covalent bond to a polar head residue of a lipid component in the composition of the present invention (see International Publication No. WO 2006/116107).

The average particle size of the complex or the lipid membrane with which the complex is enclosed in the composition of the present invention can be arbitrarily selected, if desired, and is preferably set to an average particle size described below. Examples of a method for adjusting the average particle size include an extrusion method and a method of mechanically pulverizing a large multilamellar vesicle (MLV) or the like (specifically, using Manton Gaulin, Microfluidizer, etc.) [see R. H. Muller, S. Benita and B. Bohm ed., "Emulsion and Nanosuspensions for the Formulation of Poorly Soluble Drugs", Germany, Scientific Publishers Stuttgart, 1998, p. 267-294], or the like.

The size of the complex in the composition of the present invention is preferably approximately 5 nm to 200 nm, more preferably approximately 20 nm to 150 nm, further preferably approximately 30 nm to 100 nm, in terms of an average particle size.

The size of the composition of the present invention (the lipid membrane with which the complex is enclosed) is preferably approximately 10 nm to 300 nm, more preferably approximately 30 nm to 200 nm, further preferably approximately 50 nm to 150 nm, in terms of an average particle size.

The average particle size of the complex or the lipid membrane with which the complex is enclosed in the composition of the present invention can be measured by, for example, a dynamic light scattering method.

The nucleic acid in the composition of the present invention can be introduced into a cell by introducing the composition of the present invention into a mammalian cell.

The in vivo introduction of the composition of the present invention into a mammalian cell can be performed according to procedures of transfection known in the art that can be performed in vivo. For example, the composition of the present invention can be intravenously administered to a mammal including a human and thereby delivered to, for example, an organ or a site having tumor or inflammation so that the nucleic acid in the composition of the present invention is introduced into a cell of the organ or the site that has received the composition. Examples of the organ or the site having tumor or inflammation include, but are not particularly limited to, the stomach, the large intestine, the liver, the lung, the spleen, the pancreas, the kidney, the bladder, the skin, vascular vessels, eye balls, or the like. Also, the composition of the present invention can be intravenously administered to a mammal including a human and thereby delivered to, for example, the liver, the lung, the spleen, and/or the kidney so that the nucleic acid in the composition of the present invention is introduced into a cell of the organ or the site that has received the composition. The cell of the liver, the lung, the spleen, and/or the kidney can be any of normal cells, cells related to tumor or inflammation, and cells related to the other diseases.

Provided that the nucleic acid in the composition of the present invention is a nucleic acid having a silencing effect on a target gene through the use of RNA interference (RNAi), for example, the nucleic acid silencing a target gene or the like can be introduced into a mammalian cell in vivo. As a result, the expression of the target gene can be suppressed. The recipient is preferably a human.

Provided that the target gene in the present invention is, for example, a gene expressed in the liver, the lung, the kidney, or the spleen, preferably a gene expressed in the liver, the composition of the present invention can be used as a therapeutic agent or a prophylactic agent for a disease related to the liver, the lung, the kidney, or the spleen, preferably a therapeutic agent or a prophylactic agent for a disease related to the liver. Specifically, the present invention also provides a method for treating a disease related to the liver, the lung, the kidney, or the spleen, comprising administering the composition of the present invention described above to a mammal. The recipient is preferably a human, more preferably a human having the disease related to the liver, the lung, the kidney, or the spleen.

Furthermore, the composition of the present invention can also be used as a tool for verifying the effectiveness of suppression of a target gene in an in vivo drug efficacy evaluation model as to a therapeutic agent or a prophylactic agent for a disease related to the liver, the lung, the kidney, or the spleen.

The composition of the present invention can also be used as a preparation aimed at, for example, stabilizing the nucleic acid in a biogenic substance such as a blood component (e.g., in blood, the digestive tract, of the like), reducing adverse reactions, enhancing drug accumulation to a tissue or an organ containing an expression site of the target gene, or the like.

When the composition of the present invention is pharmaceutically used as a therapeutic agent or a prophylactic agent for, for example, a disease related to the liver, the lung, the kidney, or the spleen, or the like, an administration route most effective for treatment is desirably used. Examples of such an administration route can include parenteral or oral administration such as administration into the oral cavity, intratracheal administration, intrarectal administration, subcutaneous administration, intramuscular administration, intravenous administration, or the like. Examples thereof can preferably include intravenous administration and intramuscular administration and more preferably include intravenous administration.

The dose differs depending on the pathological condition or age of the recipient, the administration route, or the like. For example, the composition of the present invention can be administered, for example, at a daily dose of approximately 0.1 µg to 1000 mg in terms of the amount of the nucleic acid.

Examples of the preparation suitable for intravenous administration or intramuscular administration include injections. A dispersion of the composition prepared by the aforementioned method may be used directly in the form of, for example, an injection or the like. Alternatively, the dispersion may be used after removal of the solvent by, for example, filtration, centrifugation, or the like, or the dispersion may be used after being freeze-dried and/or may be used after being supplemented with, for example, an excipient such as mannitol, lactose, trehalose, maltose, glycine, or the like and then freeze-dried.

In the case of an injection, the dispersion of the composition or the solvent-free or freeze-dried composition described above is preferably mixed with, for example, water, an acid, an alkali, various buffer solutions, physiological saline, an amino acid transfusion, or the like to prepare the injection. Alternatively, the injection may be prepared by the addition of, for example, an antioxidant such as citric acid, ascorbic acid, cysteine, or EDTA or a tonicity agent such as glycerin, glucose or sodium chloride. Also, the injection can also be cryopreserved by the addition of a cryopreserving agent such as glycerin.

Next, the present invention will be specifically described with reference to Examples, Reference Examples, and Test Examples. However, the present invention is not intended to be limited by these Examples, Reference Examples, and Test Examples.

Proton nuclear magnetic resonance spectra ($^1$H NMR) shown in Examples and Reference Examples were measured at 270 MHz, 300 MHz, 400 MHz, or 500 MHz, and no exchangeable proton may be clearly observed depending on compounds and measurement conditions. The multiplicity of signals is indicated as usually used.

Reference Example 1

2,2-Bis[(9Z,12Z)-octadeca-9,12-dien-1-yl]propane-1,3-diol (Compound IIc-1)

Dimethyl malonate (manufactured by Tokyo Chemical Industry Co., Ltd., 0.50 g, 3.78 mmol) was dissolved in tetrahydrofuran (20 mL). To the solution, (9Z,12Z)-octadeca-9,12-dienyl methanesulfonate (manufactured by Nu-Chek Prep, Inc., 3.26 g, 9.46 mmol), sodium hydride (manufactured by Nacalai Tesque, Inc., 60% oil, 0.454 g, 11.4 mmol), and tetrabutylammonium iodide (manufactured by Wako Pure Chemical Industries, Ltd., 0.280 g, 0.757 mmol) were added, and the mixture was stirred at 70° C. for 3 hours. A saturated aqueous solution of ammonium chloride was added to the reaction mixture, and the aqueous layer was extracted with heptane. The organic layer was washed with saturated saline, dried over anhydrous magnesium sulfate, then filtered and concentrated under reduced pressure. The obtained residue was purified with a short column to obtain a crude product of dimethyl 2,2-bis[(9Z,12Z)-octadeca-9,12-dien-1-yl]malonate.

The obtained crude product was dissolved in tetrahydrofuran (4 mL). To the solution, lithium aluminum hydride (manufactured by Tokyo Chemical Industry Co., Ltd., 0.826 g, 21.8 mmol) was added under ice cooling, and the mixture was stirred for 1 hour. The reaction was terminated by the addition of water (0.75 mL), a 15% aqueous sodium hydroxide solution (0.75 mL), and water (2.25 mL) in this order to the reaction mixture. The resulting insoluble matter was removed by filtration. The filtrate was concentrated under reduced pressure, and the obtained residue was purified by silica gel column chromatography (heptane/ethyl acetate=80/20) to obtain compound IIc-1 (1.51 g, yield: 70%).

ESI-MS m/z: 573 (M+H)$^+$

Example 1

1-Methyl-3,3-bis[(9Z,12Z)-octadeca-9,12-dien-1-yl]azetidine (Compound 1)

Step 1

Compound IIc-1 (1.00 g, 1.75 mmol) obtained in Reference Example 1 was dissolved in dichloromethane (5 mL). To the solution, pyridine (manufactured by Wako Pure Chemical Industries, Ltd., 1.41 mL, 17.5 mmol) and dimethylaminopyridine (manufactured by Nacalai Tesque, Inc., 0.0210 g, 0.175 mmol) were added. Trifluoromethanesulfonic anhydride (manufactured by Nacalai Tesque, Inc., 0.855 mL, 5.24 mmol) was added thereto under ice cooling, and the mixture was stirred for 1 hour. Water was added to the reaction mixture, followed by extraction with heptane three times. The organic layer was washed with an aqueous ammonium chloride solution and saturated saline, dried over anhydrous magnesium sulfate and filtered. The filtrate was concentrated under reduced pressure to obtain a crude product of 2,2-bis[(9Z,12Z)-octadeca-9,12-dien-1-yl]propane-1,3-diyl bis(trifluoromethanesulfonate) (1.50 g, yield: 100%).

Step 2

The crude product (0.500 g, 0.597 mmol) obtained in step 1 was dissolved in N,N-dimethylacetamide (3 mL). To the solution, methylamine (manufactured by Tokyo Chemical Industry Co., Ltd., approximately 9.8 mol/L solution in methanol, 3.05 mmol, 29.9 mmol) was added, and the mixture was stirred at 60° C. for 1 hour in an oil bath. After cooling to room temperature, water was added to the reaction mixture, followed by extraction with hexane. The organic layer was dried over anhydrous magnesium sulfate and filtered. The filtrate was concentrated under reduced pressure, and the obtained residue was purified by silica gel column chromatography (NH silica gel, hexane/ethyl acetate=100/0 to 70/30) to obtain compound 1 (0.32 g, yield: 94%).

ESI-MS m/z: 568 (M+H)$^+$; $^1$H-NMR (CDCl$_3$) δ: 0.89 (6H, t, J=6.8 Hz), 1.12-1.38 (36H, m), 1.48-1.55 (4H, m), 2.05 (8H, q, J=6.8 Hz), 2.30 (3H, s), 2.78 (4H, t, J=6.8 Hz), 2.93 (4H, s), 5.29-5.43 (8H, m).

Example 2

3,3-Bis[(9Z,12Z)-octadeca-9,12-dien-1-yl]-1-propylazetidine (Compound 2)

Step 1

Compound IIc-1 (3.50 g, 6.11 mmol) obtained in Reference Example 1 was dissolved in dichloromethane (15 mL). To the solution, triethylamine (manufactured by Wako Pure Chemical Industries, Ltd., 2.55 mL, 18.3 mmol) and mesyl chloride (manufactured by Tokyo Chemical Industry Co., Ltd., 1.12 mL, 15.3 mmol) were added under ice cooling, and the mixture was stirred for 1 hour. Water was added to the reaction mixture, followed by extraction with heptane. The organic layer was washed with saturated saline, dried over anhydrous magnesium sulfate and filtered. The filtrate was concentrated under reduced pressure, and the obtained residue was purified by silica gel column chromatography (chloroform/methanol=100/0 to 97/3) to obtain 2,2-bis[(9Z,12Z)-octadeca-9,12-dien-1-yl]propane-1,3-diyl dimethanesulfonate (3.30 g, yield: 74%).

Step 2

2,2-Bis[(9Z,12Z)-octadeca-9,12-dien-1-yl]propane-1,3-diyl dimethanesulfonate (0.200 g, 0.274 mmol) obtained in step 1 was dissolved in N,N-dimethylacetamide (0.5 mL). To the solution, propylamine (0.451 mL, 5.49 mmol) was added, and the mixture was stirred at 130° C. for 6 hours using a microwave reaction apparatus. Water was added to the reaction mixture, followed by extraction with heptane. The organic layer was washed with saturated saline, dried over anhydrous magnesium sulfate and filtered. The filtrate was concentrated under reduced pressure, and the obtained residue was purified by silica gel column chromatography (NH silica gel, heptane/ethyl acetate=100/0 to 80/20) to obtain compound 2 (14.8 mg, yield: 9%).

ESI-MS m/z: 597 (M+H)$^+$; $^1$H-NMR (CDCl$_3$) δ: 0.84-0.92 (9H, m), 1.11-1.41 (38H, m), 1.49-1.56 (4H, m), 2.05 (8H, q, J=6.6 Hz), 2.36 (2H, t, J=7.7 Hz), 2.77 (4H, t, J=5.9 Hz), 2.90 (4H, s), 5.27-5.45 (8H, m).

Example 3

3,3-Bis[(9Z,12Z)-octadeca-9,12-dien-1-yl]azetidine (Compound 3)

Compound 3 (0.0750 g, yield: 23%) was obtained in the same way as in Example 1 by using ammonia (manufactured by Sigma-Aldrich Corp., approximately 7 mol/L solution in methanol, 4.27 mL, 29.9 mmol) instead of methylamine.

ESI-MS m/z: 554 (M+H)$^+$; $^1$H-NMR (CDCl$_3$) δ: 0.89 (6H, t, J=7.0 Hz), 1.12-1.38 (36H, m), 1.53-1.58 (4H, m), 2.05 (8H, q, J=6.8 Hz), 2.78 (4H, t, J=6.8 Hz), 3.28 (4H, s), 5.31-5.41 (8H, m).

Example 4

3-(Dimethylamino)propyl 3,3-bis[(9Z,12Z)-octadeca-9,12-dien-1-yl]azetidine-1-carboxylate (Compound 4)

Compound 3 obtained in Example 3 was dissolved in acetonitrile (2 mL). To the solution, 3-(dimethylamino) propyl 4-nitrophenylcarbonate hydrochloride (compound VII-1) (0.0620 g, 0.203 mmol) synthesized by a method equivalent to the method described in "J. Am. Chem. Soc.", 1981, Vol. 103, p. 4194-4199 and triethylamine (0.0570 mL, 0.406 mmol) were added, and the mixture was stirred at 80° C. for 2 hours. The reaction mixture was diluted with ethyl acetate and washed with water. The organic layer was dried over anhydrous magnesium sulfate, then filtered and concentrated under reduced pressure. The obtained residue was purified by silica gel column chromatography (NH silica gel, hexane/ethyl acetate=80/20) to obtain compound 4 (0.0580 g, yield: 63%).

ESI-MS m/z: 683 (M+H)$^+$; $^1$H-NMR (CDCl$_3$) δ: 0.89 (6H, t, J=6.8 Hz), 1.13-1.22 (4H, m), 1.25-1.39 (32H, m), 1.49-1.55 (4H, m), 1.73-1.81 (2H, m), 2.05 (8H, q, J=6.8 Hz), 2.22 (6H, s), 2.33 (2H, t, J=7.6 Hz), 2.77 (4H, t, J=6.8 Hz), 3.58 (4H, s), 4.08 (2H, t, J=6.5 Hz), 5.29-5.42 (8H, m).

Reference Example 2

2,2-Bis[(Z)-octadec-9-en-1-yl]propane-1,3-diol (Compound IIc-2)

Compound IIc-2 (1.06 g, yield: 35%) was obtained in the same way as in Reference Example 1 by using (Z)-octadec-9-en-1-yl methanesulfonate (manufactured by Nu-Chek Prep, Inc., 4.50 g, 13.0 mmol) instead of (9Z,12Z)-octadeca-9,12-dienyl methanesulfonate.

ESI-MS m/z: 577 (M+H)$^+$

Example 5

1-Methyl-3,3-bis[(Z)-octadec-9-en-1-yl]azetidine (Compound 5)

Compound 5 (0.272 g, yield: 92%) was obtained in the same way as in Example 1 by using compound IIc-2 (0.300 g, 0.520 mmol) obtained in Reference Example 2 instead of compound IIc-1 obtained in Reference Example 1.

ESI-MS m/z: 572 (M+H)$^+$; $^1$H-NMR (CDCl$_3$) δ: 0.88 (6H, t, J=6.8 Hz), 1.14-1.35 (48H, m), 1.50-1.53 (4H, m), 2.02 (8H, q, J=6.8 Hz), 2.31 (3H, s), 2.94 (4H, s), 5.31-5.39 (4H, m).

Reference Example 3

2,2-Bis[(Z)-hexadec-9-en-1-yl]propane-1,3-diol (Compound IIc-3)

Compound IIc-3 (2.07 g, yield: 59%) was obtained in the same way as in Reference Example 1 by using (Z)-hexadec-9-en-1-yl methanesulfonate (manufactured by Nu-Chek Prep, Inc., 5.00 g, 15.7 mmol) instead of (9Z,12Z)-octadeca-9,12-dienyl methanesulfonate.

ESI-MS m/z: 521 (M+H)$^+$

Example 6

3,3-Bis[(Z)-hexadec-9-en-1-yl]-1-methylazetidine (Compound 6)

Compound 6 (0.263 g, yield: 89%) was obtained in the same way as in Example 1 by using compound IIc-3 (0.300 g, 0.576 mmol) obtained in Reference Example 3 instead of compound IIc-1 obtained in Reference Example 1.

ESI-MS m/z: 516 (M+H)⁺; ¹H-NMR (CDCl₃) δ: 0.89 (6H, t, J=6.8 Hz), 1.14-1.35 (40H, m), 1.50-1.53 (4H, m), 2.02 (8H, q, J=6.8 Hz), 2.31 (3H, s), 2.94 (4H, s), 5.31-5.39 (4H, m).

Reference Example 4

2,2-Bis[(11Z,14Z)-icosa-11,14-dien-1-yl]propane-1,3-diol (Compound IIc-4)

Compound IIc-4 (2.07 g, yield: 59%) was obtained in the same way as in Reference Example 1 by using (11Z,14Z)-icosa-11,14-dien-1-yl methanesulfonate (manufactured by Nu-Chek Prep, Inc., 5.00 g, 13.4 mmol) instead of (9Z,12Z)-octadeca-9,12-dienyl methanesulfonate.
ESI-MS m/z: 629 (M+H)⁺

Example 7

3,3-Bis[(11Z,14Z)-icosa-11,14-dien-1-yl]-1-methylazetidine (Compound 7)

Compound 7 (0.256 g, yield: 86%) was obtained in the same way as in Example 1 by using compound IIc-4 (0.300 g, 0.477 mmol) obtained in Reference Example 4 instead of compound IIc-1 obtained in Reference Example 1.
ESI-MS m/z: 624 (M+H)⁺; ¹H-NMR (CDCl₃) δ: 0.89 (6H, t, J=6.4 Hz), 1.16-1.37 (44H, m), 1.50-1.54 (4H, m), 2.05 (8H, q, J=6.8 Hz), 2.31 (3H, s), 2.78 (4H, t, J=6.4 Hz), 2.94 (4H, s), 5.30-5.42 (8H, m).

Example 8

3-(3,3-di((9Z,12Z)-Octadeca-9,12-dien-1-yl)azetidin-1-yl)propan-1-ol (Compound 8)

Compound 8 (0.237 g, yield: 63%) was obtained in the same way as in Example 1 by using 3-aminopropan-1-ol (manufactured by Tokyo Chemical Industry Co., Ltd., 0.468 mL, 6.16 mmol) instead of methylamine.
ESI-MS m/z: 613 (M+H)⁺; ¹H-NMR (CDCl₃) δ: 0.89 (6H, t, J=6.8 Hz), 1.13-1.39 (40H, m), 1.50-1.56 (2H, m), 2.05 (8H, q, J=6.8 Hz), 2.69 (2H, t, J=5.4 Hz), 2.77 (4H, t, J=6.3 Hz), 2.93 (4H, s), 3.75 (2H, t, J=5.4 Hz), 5.27-5.44 (8H, m).

Example 9

2-(3,3-di((9Z,12Z)-Octadeca-9,12-dien-1-yl)azetidin-1-yl)ethan-1-ol (Compound 9)

Compound 9 (0.012 g, yield: 13%) was obtained in the same way as in Example 2 by using 2-aminoethanol (manufactured by Tokyo Chemical Industry Co., Ltd., 0.800 g, 13.1 mmol) instead of methylamine.
ESI-MS m/z: 598 (M+H)⁺; ¹H-NMR (CDCl₃) δ: 0.89 (6H, t, J=6.8 Hz), 1.14-1.42 (40H, m), 2.05 (8H, q, J=6.5 Hz), 2.59 (2H, t, J=5.3 Hz), 2.77 (4H, t, J=5.9 Hz), 2.96 (4H, s), 3.48 (2H, t, J=5.3 Hz), 5.28-5.44 (8H, m).

Reference Example 5

2-Decyl-2-((9Z,12Z)-octadeca-9,12-dien-1-yl)propane-1,3-diol (Compound IIc-5)

Step 1
Dimethyl malonate (0.400 g, 3.03 mmol) was dissolved in acetonitrile (10 mL). To the solution, (9Z,12Z)-octadeca-9,12-dienyl methanesulfonate (1.25 g, 3.63 mmol), cesium carbonate (manufactured by Wako Pure Chemical Industries, Ltd., 1.97 g, 6.06 mmol), and tetrabutylammonium iodide (1.34 g, 3.63 mmol) were added, and the mixture was stirred at 60° C. for 1 hour. Water was added to the reaction mixture, and the aqueous layer was extracted with hexane. The organic layer was washed with saturated saline, dried over anhydrous magnesium sulfate, then filtered and concentrated under reduced pressure. The obtained residue was purified by column chromatography (hexane/ethyl acetate=90/10) to obtain dimethyl 2-((9Z,12Z)-octadeca-9,12-dien-1-yl)malonate (0.800 g, yield: 69%).
ESI-MS m/z: 381 (M+H)⁺
Step 2
Dimethyl 2-((9Z,12Z)-octadeca-9,12-dien-1-yl)malonate (0.400 g, 1.05 mmol) obtained in step 1 was dissolved in tetrahydrofuran (2 mL). To the solution, 1-bromodecane (manufactured by Tokyo Chemical Industry Co., Ltd., 0.326 g, 1.58 mmol), sodium hydride (60% oil, 0.063 g, 1.58 mmol), and tetrabutylammonium iodide (0.280 g, 0.757 mmol) were added, and the mixture was stirred at 70° C. for 3 hours. Water was added to the reaction mixture, and the aqueous layer was extracted with hexane. The organic layer was washed with saturated saline, dried over anhydrous magnesium sulfate and then filtered. The filtrate was concentrated under reduced pressure to obtain a crude product of dimethyl 2-decyl-2-((9Z,12Z)-octadeca-9,12-dien-1-yl)malonate.

The obtained crude product was dissolved in tetrahydrofuran (3 mL). To the solution, lithium aluminum hydride (0.122 g, 3.23 mmol) was added under ice cooling, and the mixture was stirred for 1 hour. The reaction was terminated by the addition of water (0.1 mL), a 15% aqueous sodium hydroxide solution (0.1 mL), and water (0.3 mL) in this order to the reaction mixture. The resulting insoluble matter was removed by filtration. The filtrate was concentrated under reduced pressure, and the obtained residue was purified by silica gel column chromatography (hexane/ethyl acetate=90/10 to 50/50) to obtain compound IIc-5 (0.265 g, yield: 53%).
ESI-MS m/z: 465 (M+H)⁺

Example 10

3-Decyl-1-methyl-3-((9Z,12Z)-octadeca-9,12-dien-1-yl)azetidine (Compound 10)

Compound 10 (0.206 g, yield: 79%) was obtained in the same way as in Example 1 by using compound IIc-5 (0.265 g, 0.570 mmol) obtained in Reference Example 5 instead of compound IIc-1 obtained in Reference Example 1.
ESI-MS m/z: 460 (M+H)⁺; ¹H-NMR (CDCl₃) δ: 0.84-0.93 (6H, m), 1.11-1.40 (34, m), 1.50-1.55 (4H, m), 2.05 (4H, q, J=6.8 Hz), 2.30 (3H, s), 2.77 (2H, t, J=6.5 Hz), 2.93 (4H, s), 5.29-5.43 (4H, m).

Example 11

3-(3,3-di((9Z,12Z)-Octadeca-9,12-dien-1-yl)azetidin-1-yl)-N,N-dimethylpropan-1-amine (Compound 11)

Compound 11 (0.091 g, yield: 34%) was obtained in the same way as in Example 1 by using N,N-dimethyl-1,3- propanediamine (manufactured by Tokyo Chemical Industry Co., Ltd., 0.427 mL, 4.18 mmol) instead of methylamine.

ESI-MS m/z: 639 (M+H)⁺; ¹H-NMR (CDCl₃) δ: 0.86 (6H, t, J=7.0 Hz), 1.08-1.18 (4H, m), 1.21-1.38 (32H, m), 1.56-1.60 (4H, m), 1.61-1.69 (2H, m), 2.01 (8H, q, J=6.8 Hz), 2.21 (6H, s), 2.31 (2H, t, J=7.1 Hz), 2.65-2.72 (2H, m), 2.75 (4H, t, J=6.7 Hz), 3.20 (4H, s), 5.25-5.40 (8H, m).

Example 12

2-(3,3-di((9Z,12Z)-Octadeca-9,12-dien-1-yl)azetidin-1-yl)-N,N-dimethylethan-1-amine (Compound 12)

Compound 12 (0.312 g, yield: 77%) was obtained in the same way as in Example 1 by using N,N-dimethylethylenediamine (manufactured by Tokyo Chemical Industry Co., Ltd., 0.709 mL, 6.51 mmol) instead of methylamine.

ESI-MS m/z: 625 (M+H)⁺; ¹H-NMR (CDCl₃) δ: 0.89 (6H, t, J=7.0 Hz), 1.11-1.20 (4H, m), 1.23-1.39 (32H, m), 1.49-1.55 (4H, m), 2.05 (8H, q, J=6.8 Hz), 2.21 (6H, s), 2.22-2.26 (2H, m), 2.52-2.58 (2H, m), 2.77 (4H, t, J=6.7 Hz), 2.93 (4H, s), 5.28-5.43 (8H, m).

Reference Example 6

2-((9Z,12Z)-Octadeca-9,12-dien-1-yl)-2-octadecylpropane-1,3-diol (Compound IIc-6)

Compound IIc-6 (0.186 g, overall yield: 28%) was obtained in the same way as in Reference Example 5 by using 1-bromooctadecane (manufactured by Tokyo Chemical Industry Co., Ltd., 0.394 g, 1.18 mmol) instead of 1-bromodecane.

ESI-MS m/z: 577 (M+H)⁺

Example 13

1-Methyl-3-((9Z,12Z)-octadeca-9,12-dien-1-yl)-3-octadecylazetidine (Compound 13)

Compound 13 (0.030 g, yield: 16%) was obtained in the same way as in Example 1 by using compound IIc-6 (0.186 g, 0.322 mmol) obtained in Reference Example 6 instead of compound IIc-1 obtained in Reference Example 1.

ESI-MS m/z: 572 (M+H)⁺; ¹H-NMR (CDCl₃) δ: 0.84-0.90 (6H, m), 1.10-1.22 (4H, m), 1.23-1.38 (46H, m), 1.56-1.62 (4H, m), 2.04 (4H, q, J=6.8 Hz), 2.51 (3H, s), 2.76 (2H, t, J=6.7 Hz), 3.25 (4H, s), 5.28-5.42 (4H, m).

Reference Example 7

1-((2-Nitrophenyl)sulfonyl)-3,3-bis(2-(((9Z,12Z)-octadeca-9,12-dien-1-yl)oxy)ethyl)azetidine (Compound XIIIf-1)

Step 1

2-((9Z,12Z)-Octadeca-9,12-dien-1-yloxy)ethanol (2.30 g, 7.41 mmol) synthesized by the method described in International Publication No. WO 2012/108397 was dissolved in dichloromethane (20 mL). To the solution, triethylamine (1.55 mL, 11.1 mmol) and 2-nitrobenzene-1-sulfonyl chloride (2.13 g, 9.63 mmol) were added under ice cooling, and the mixture was stirred for 2 hours. Water was added to the reaction mixture, and the aqueous layer was extracted with ethyl acetate. The organic layer was washed with saturated saline, dried over anhydrous magnesium sulfate, then filtered and concentrated under reduced pressure. The obtained residue was purified by column chromatography (hexane/ethyl acetate=90/10) to obtain 2-((9Z,12Z)-octadeca-9,12-dien-1-yloxy)ethyl 2-nitrobenzenesulfonate (1.93 g, yield: 53%).

ESI-MS m/z: 496 (M+H)⁺

Step 2

2-((9Z,12Z)-Octadeca-9,12-dien-1-yloxy)ethyl 2-nitrobenzenesulfonate (1.93 g, 3.89 mmol) obtained in step 1 was dissolved in N,N-dimethylformamide (8 mL). To the solution, ethyl 2-cyanoacetate (manufactured by Tokyo Chemical Industry Co., Ltd., 0.189 ml, 1.77 mmol) and cesium carbonate (1.73 g, 5.30 mmol) were added, and the mixture was stirred at 100° C. for 1 hour. Water was added to the reaction mixture, and the aqueous layer was extracted with hexane. The organic layer was washed with saturated saline, dried over anhydrous magnesium sulfate and then filtered. The filtrate was concentrated under reduced pressure to obtain a crude product of ethyl 2-cyano-4-(((9Z,12Z)-octadeca-9,12-dien-1-yl)oxy)-2-(2-(((9Z,12Z)-octadeca-9,12-dien-1-yl)oxy)ethyl)butanoate.

The obtained crude product was dissolved in tetrahydrofuran (8 mL). To the solution, lithium aluminum hydride (0.239 g, 6.30 mmol) was added under ice cooling, and the mixture was stirred at room temperature for 1 hour. The reaction was terminated by the addition of water (0.24 mL), a 15% aqueous sodium hydroxide solution (0.24 mL), and water (0.72 mL) in this order to the reaction mixture. The resulting insoluble matter was removed by filtration. The filtrate was concentrated under reduced pressure, and the obtained residue was purified by silica gel column chromatography (hexane/ethyl acetate=99/1 to 50/50) to obtain 2-(aminoethyl)-4-(((9Z,12Z)-octadeca-9,12-dien-1-yl)oxy)-2-(2-(((9Z,12Z)-octadeca-9,12-dien-1-yl)oxy)ethyl)butan-1-ol (0.350 g, yield: 34%).

ESI-MS m/z: 660 (M+H)⁺

Step 3

2-(Aminoethyl)-4-(((9Z,12Z)-octadeca-9,12-dien-1-yl)oxy)-2-(2-(((9Z,12Z)-octadeca-9,12-dien-1-yl)oxy)ethyl)butan-1-ol (0.53 g, 0.803 mmol) obtained in Step 2 was dissolved in dichloromethane (4 mL). To the solution, triethylamine (0.168 mL, 1.20 mmol) and 2-nitrobenzene-1-sulfonyl chloride (0.231 g, 1.04 mmol) were added under ice cooling, and the mixture was stirred for 1 hour. Water was added to the reaction mixture, and the aqueous layer was extracted with hexane. The organic layer was washed with water and saturated saline, dried over anhydrous magnesium sulfate and then filtered. The filtrate was concentrated to obtain a crude product of N-(2-(hydroxymethyl)-4-(((9Z,12Z)-octadeca-9,12-dien-1-yl)oxy)-2-(2-(((9Z,12Z)-octadeca-9,12-dien-1-yl)oxy)ethyl)butyl)-2-nitrobenzenesulfonamide.

The obtained crude product was dissolved in tetrahydrofuran (4 mL). To the solution, triphenylphosphine (manufactured by Nacalai Tesque, Inc., 0.340 g, 1.30 mmol) and diisopropyl azodicarboxylate (manufactured by Tokyo Chemical Industry Co., Ltd., 40% solution in toluene, 1.9 mol/L, 0.682 mL, 1.30 mmol) were added, and the mixture was stirred at room temperature for 15 minutes. Water was added to the reaction mixture, and the aqueous layer was extracted with hexane. The organic layer was washed with saturated saline, dried over anhydrous magnesium sulfate, then filtered and concentrated under reduced pressure. The obtained residue was purified by silica gel column chromatography (hexane/ethyl acetate=95/5 to 70/30) to obtain compound XIIIf-1 (0.585 g, yield: 82%).

ESI-MS m/z: 827 (M+H)⁺

Example 14

3,3-Bis(2-(((9Z,12Z)-octadeca-9,12-dien-1-yl)oxy)ethyl)azetidine (Compound 14)

Compound XIIIf-1 (0.585 g, 0.707 mmol) obtained in Reference Example 7 was dissolved in acetonitrile (7 mL). To the solution, 1-dodecanethiol (manufactured by Tokyo Chemical Industry Co., Ltd., 0.412 mL, 1.77 mmol) and 1,8-diazabicyclo[5.4.0]-7-undecene (manufactured by Nacalai Tesque, Inc., 0.246 mL, 1.77 mmol) were added, and the mixture was stirred at 70° C. for 1 hour. Water was added to the reaction mixture, and the aqueous layer was extracted with hexane. The organic layer was washed with saturated saline, dried over anhydrous magnesium sulfate, then filtered and concentrated under reduced pressure. The obtained residue was purified by NH silica gel column chromatography (hexane/ethyl acetate=99/1 to 30/70) to obtain compound 14 (0.045 g, yield: 10%).

ESI-MS m/z: 642 (M+H)$^+$; $^1$H-NMR (CDCl$_3$) δ: 0.89 (6H, t, J=7.0 Hz), 1.24-1.39 (32H, m), 1.50-1.57 (4H, m), 1.91 (4H, t, J=7.0 Hz), 2.05 (8H, q, J=6.9 Hz), 2.77 (4H, t, J=6.6 Hz), 3.38 (4H, t, J=6.7 Hz), 3.41 (4H, s), 3.46 (4H, t, J=7.0 Hz), 5.28-5.44 (8H, m).

Example 15

1-Methyl-3,3-bis(2-(((9Z,12Z)-octadeca-9,12-dien-1-yl)oxy)ethyl)azetidine (Compound 15)

Compound 14 (0.134 g, 0.209 mmol) obtained in Example 14 was dissolved in 1,2-dichloroethane (1 mL) and methanol (1 mL). To the solution, formaldehyde (manufactured by Wako Pure Chemical Industries, Ltd., 37% aqueous solution, 0.076 mL, 1.04 mmol) and sodium triacetoxyborohydride (manufactured by Tokyo Chemical Industry Co., Ltd., 0.111 g, 0.522 mmol) were added, and the mixture was stirred overnight at room temperature. A saturated aqueous solution of sodium bicarbonate was added to the reaction mixture, and the aqueous layer was extracted with chloroform. The organic layer was dried over anhydrous magnesium sulfate, then filtered and concentrated under reduced pressure. The obtained residue was purified by NH silica gel column chromatography (hexane/ethyl acetate=90/10) to obtain compound 15 (0.088 g, yield: 64%).

ESI-MS m/z: 656 (M+H)$^+$; $^1$H-NMR (CDCl$_3$) δ: 0.89 (6H, t, J=6.8 Hz), 1.24-1.40 (32H, m), 1.49-1.57 (4H, m), 1.87 (4H, t, J=6.8 Hz), 2.05 (8H, q, J=6.9 Hz), 2.30 (3H, s), 2.77 (4H, t, J=6.3 Hz), 3.04 (4H, s), 3.37 (4H, t, J=6.7 Hz), 3.44 (4H, t, J=7.0 Hz), 5.28-5.44 (8H, m).

Reference Example 8

1-((2-Nitrophenyl)sulfonyl)-3,3-bis(3-(((9Z,12Z)-octadeca-9,12-dien-1-yl)oxy)propyl)azetidine (Compound XIIIf-2)

Step 1

(9Z,12Z)-Octadeca-9,12-dienyl methanesulfonate (10.0 g, 29.0 mmol) was dissolved in 1,4-dioxane (20 mL). To the solution, 1,3-propanediol (manufactured by Wako Pure Chemical Industries, Ltd., 55.2 g, 726 mmol) was added, and the mixture was stirred for 2 days under heating to reflux. Water was added to the reaction mixture, and the aqueous layer was extracted with chloroform. The organic layer was washed with saturated saline, dried over anhydrous magnesium sulfate, then filtered and concentrated under reduced pressure. The obtained residue was purified by silica gel column chromatography (hexane/ethyl acetate=90/10) to obtain 3-((9Z,12Z)-octadeca-9,12-dien-1-yloxy)propan-1-ol (4.96 g, yield: 53%).

ESI-MS m/z: 324 (M+H)$^+$

Step 2

3-((9Z,12Z)-Octadeca-9,12-dien-1-yloxy)propan-1-ol (4.95 g, 15.3 mmol) obtained in step 1 was dissolved in dichloromethane (20 mL). To the solution, triethylamine (4.25 mL, 30.5 mmol) and mesylic chloride (2.36 mL, 30.5 mmol) were added under ice cooling, and the mixture was stirred at 0° C. for 2 hours. Water was added to the reaction mixture, and the aqueous layer was extracted with ethyl acetate. The organic layer was washed with saturated saline, dried over anhydrous magnesium sulfate, then filtered and concentrated under reduced pressure. The obtained residue was purified by silica gel column chromatography (hexane/ethyl acetate=90/10) to obtain 3-((9Z,12Z)-octadeca-9,12-dien-1-yloxy)propyl methanesulfonate (5.47 g, yield: 89%).

ESI-MS m/z: 403 (M+H)$^+$

Step 3

Compound XIIIf-2 (0.109 g, overall yield: 7.6%) was obtained in the same way as in steps 2 and 3 of Reference Example 7 by using 3-((9Z,12Z)-octadeca-9,12-dien-1-yloxy)propyl methanesulfonate (1.57 g, 3.89 mmol) obtained in step 2 instead of 2-((9Z,12Z)-octadeca-9,12-dien-1-yloxy)ethyl 2-nitrobenzenesulfonate.

ESI-MS m/z: 855 (M+H)$^+$

Example 16

3,3-Bis(3-(((9Z,12Z)-octadeca-9,12-dien-1-yl)oxy)propyl)azetidine (Compound 16)

Compound 16 (0.062 g, yield: 69%) was obtained in the same way as in Example 14 by using compound XIIIf-2 (0.109 g, 0.135 mmol) instead of compound XIIIf-1.

ESI-MS m/z: 670 (M+H)$^+$; $^1$H-NMR (CDCl$_3$) δ: 0.89 (6H, t, J=7.0 Hz), 1.22-1.40 (32H, m), 1.44-1.67 (12H, m), 2.05 (8H, q, J=6.8 Hz), 2.77 (4H, t, J=6.7 Hz), 3.31 (4H, s), 3.39 (8H, t, J=6.7 Hz), 5.28-5.45 (8H, m).

Example 17

1-Methyl-3,3-bis(3-(((9Z,12Z)-octadeca-9,12-dien-1-yl)oxy)propyl)azetidine (Compound 17)

Compound 17 (0.056 g, yield: 88%) was obtained in the same way as in Example 15 by using compound 16 (0.062 g, 0.093 mmol) instead of compound 14.

ESI-MS m/z: 684 (M+H)$^+$; $^1$H-NMR (CDCl$_3$) δ: 0.89 (6H, t, J=6.8 Hz), 1.23-1.40 (32H, m), 1.42-1.62 (12H, m), 2.05 (8H, q, J=6.9 Hz), 2.31 (3H, s), 2.77 (4H, t, J=6.7 Hz), 2.96 (4H, s), 3.35-3.43 (8H, m), 5.25-5.47 (8H, m).

Example 18

2-Dimethyl-3,3-di((9Z,12Z)-octadeca-9,12-dien-1-yl)azetidine (Compound 18)

Step 1

Ethyl cyanoacetate (2.00 g, 17.7 mmol) was dissolved in acetonitrile (50 mL). To the solution, (9Z,12Z)-octadeca-9,12-dienyl methanesulfonate (13.4 g, 38.9 mmol) and cesium carbonate (17.3 g, 53.1 mmol) were added, and the mixture was stirred at 60° C. for 2 hours. Water was added to the reaction mixture, and the aqueous layer was extracted with hexane. The organic layer was washed with saturated saline, dried over anhydrous magnesium sulfate and then filtered. The filtrate was concentrated under reduced pressure to obtain a crude product of ethyl (11Z,14Z)-2-cyano-2-((9Z,12Z)-octadeca-9,12-dien-1-yl)icosa-11,14-dienoate.

The obtained crude product was dissolved in tetrahydrofuran (5 mL). To the solution, lithium aluminum hydride (2.49 g, 65.6 mmol) was added under ice cooling, and the mixture was stirred for 30 minutes. The reaction was terminated by the addition of water (2.5 mL), a 15% aqueous sodium hydroxide solution (2.5 mL), and water (7.5 mL) in this order to the reaction mixture. The resulting insoluble matter was removed by filtration. The filtrate was concentrated under reduced pressure, and the obtained residue was purified by silica gel column chromatography (chloroform/methanol=99/1 to 90/10) to obtain (11Z,14Z)-2-(aminoethyl)-2-((9Z,12Z)-octadeca-9,12-dien-1-yl)icosa-11,14-dien-1-ol (2.50 g, yield: 25%).

ESI-MS m/z: 572 (M+H)$^+$

Step 2

(11Z,14Z)-2-(Aminoethyl)-2-((9Z,12Z)-octadeca-9,12-dien-1-yl)icosa-11,14-dien-1-ol (2.50 g, 4.37 mmol) obtained in step 1 was dissolved in tetrahydrofuran (20 mL). To the solution, triethylamine (1.83 mL, 13.1 mmol) and tert-butyl dicarbonate (manufactured by Watanabe Chemical Industries, Ltd., 1.12 mL, 4.81 mmol) were added, and the mixture was stirred overnight at room temperature. The reaction mixture was concentrated under reduced pressure, and the obtained residue was purified by silica gel column chromatography (hexane/ethyl acetate=95/5) to obtain tert-butyl ((11Z,14Z)-2-(hydroxymethyl)-2-((9Z,12Z)-octadeca-9,12-dien-1-yl)icosa-11,14-dien-1-yl)carbamate (2.65 g, yield: 90%).

ESI-MS m/z: 672 (M+H)$^+$

Step 3 tert-Butyl ((11Z,14Z)-2-(hydroxymethyl)-2-((9Z,12Z)-octadeca-9,12-dien-1-yl)icosa-11,14-dien-1-yl)carbamate (2.10 g, 3.12 mmol) obtained in step 2 was dissolved in dichloromethane (10 mL). To the solution, a Dess-Martin reagent (manufactured by Tokyo Chemical Industry Co., Ltd., 1.72 g, 4.06 mmol) was added under ice cooling, and the mixture was stirred at room temperature for 2 hours. Water was added to the reaction mixture, followed by extraction with hexane. The organic layer was washed with saturated saline, dried over anhydrous magnesium sulfate, then filtered and concentrated under reduced pressure. The obtained residue was purified by silica gel column chromatography (hexane/ethyl acetate=100/0 to 80/20) to obtain tert-butyl ((11Z,14Z)-2-formyl-2-((9Z,12Z)-octadeca-9,12-dien-1-yl)icosa-11,14-dien-1-yl)carbamate (2.00 g, yield: 96%).

ESI-MS m/z: 670 (M+H)$^+$

Step 4 tert-Butyl ((11Z,14Z)-2-formyl-2-((9Z,12Z)-octadeca-9,12-dien-1-yl)icosa-11,14-dien-1-yl)carbamate (0.432 g, 0.645 mmol) obtained in step 3 was dissolved in tetrahydrofuran (2 mL). To the solution, methyl magnesium bromide (manufactured by Kanto Chemical Co., Inc., 3 mol/L, 0.258 mL, 0.774 mmol) was added under ice cooling. Then, the mixture was cooled to −50° C. Methyl magnesium bromide (3 mol/L, 0.150 mL, 0.451 mmol) was added thereto, and the mixture was stirred for 1 hour. The reaction was terminated by the addition of a saturated aqueous solution of ammonium chloride to the reaction mixture, followed by extraction with ethyl acetate. The organic layer was washed with saturated saline, dried over anhydrous magnesium sulfate, then filtered and concentrated under reduced pressure. The obtained residue was purified by silica gel column chromatography (hexane/ethyl acetate=95/5 to 50/50) to obtain tert-butyl ((11Z,14Z)-2-(1-hydroxyethyl)-2-((9Z,12Z)-octadeca-9,12-dien-1-yl)icosa-11,14-dien-1-yl)carbamate (0.200 g, yield: 45%).

ESI-MS m/z: 686 (M+H)$^+$

Step 5 tert-Butyl ((11Z,14Z)-2-(1-hydroxyethyl)-2-((9z,12Z)-octadeca-9,12-dien-1-yl)icosa-11,14-dien-1-yl)carbamate (0.290 g, 0.423 mmol) obtained in step 4 was dissolved in dichloromethane (2 mL). To the solution, pyridine (0.171 mL, 2.11 mmol) and mesyl chloride (0.049 mL, 0.634 mmol) were added under ice cooling, and the mixture was stirred at 0° C. for 30 minutes. The reaction was completed by the further addition of pyridine (0.171 mL, 2.11 mmol) and mesyl chloride (0.098 mL, 1.27 mmol) in this order. Water was added to the reaction mixture, and the aqueous layer was extracted with ethyl acetate. The organic layer was washed with saturated saline, dried over anhydrous magnesium sulfate and then filtered. The obtained filtrate was concentrated under reduced pressure to obtain a crude product of (12Z,15Z)-3-(((tert-butoxycarbonyl)amino)methyl)-3-((9z,12Z)-octadeca-9,12-dien-1-yl)henicosa-12,15-dien-2-yl methanesulfonate.

The obtained crude product was dissolved in N,N-dimethylformamide (8 mL). To the solution, sodium hydride (60% oil, 8 mg, 0.335 mmol) was added under ice cooling. Then, the mixture was stirred at 50° C. for 1 hour and stirred overnight at room temperature. A saturated aqueous solution of ammonium chloride was added to the reaction mixture, and the aqueous layer was extracted with ethyl acetate. The organic layer was washed with saturated saline, dried over anhydrous magnesium sulfate, then filtered and concentrated under reduced pressure. The obtained residue was purified by silica gel column chromatography (hexane/ethyl acetate=95/5 to 50/50) to obtain tert-butyl 2-methyl-3,3-di((9Z,12Z)-octadeca-9,12-dien-1-yl)azetidine-1-carboxylate (0.070 g, yield: 31%).

ESI-MS m/z: 668 (M+H)$^+$

Step 6 tert-Butyl 2-methyl-3,3-di((9Z,12Z)-octadeca-9,12-dien-1-yl)azetidine-1-carboxylate (0.090 g, 0.135 mmol) obtained in Step 5 was dissolved in dichloromethane (2 mL). To the solution, trifluoroacetic acid (0.500 mL, 6.49 mmol) was added under ice cooling, and the mixture was stirred at 0° C. for 30 minutes. A saturated aqueous solution of sodium bicarbonate was added to the reaction mixture, followed by extraction with chloroform. The organic layer was dried over anhydrous magnesium sulfate, then filtered and concentrated under reduced pressure. The obtained residue was purified by NH silica gel column chromatography (chloroform/methanol=100/0 to 90/10) to obtain compound 18 (0.030 g, yield: 39%).

ESI-MS m/z: 568 (M+H)$^+$

Example 19

1,2-Dimethyl-3,3-di((9Z,12Z)-octadeca-9,12-dien-1-yl)azetidine (Compound 19)

Compound 19 (0.020 g, yield: 65%) was obtained in the same way as in Example 15 by using compound 18 (0.030 g, 0.053 mmol) instead of compound 14.

ESI-MS m/z: 582 (M+H)$^+$; $^1$H-NMR (CDCl$_3$) δ: 0.89 (6H, t, J=6.8 Hz), 1.03 (3H, d, J=6.6 Hz), 1.07-1.65 (40H, m), 2.05 (8H, q, J=6.8 Hz), 2.27 (3H, s), 2.39 (1H, d, J=6.8 Hz), 2.69-2.81 (5H, m), 3.21 (1H, d, J=6.6 Hz), 5.28-5.44 (8H, m).

Reference Example 9

2-((9Z,12Z)-Octadeca-9,12-dien-1-yl)-2-((((9Z,12Z)-octadeca-9,12-dien-1-yl)oxy)methyl)propane-1,3-diol (Compound IIc-7)

Step 1

2-((9Z,12Z)-Octadeca-9,12-dien-1-yl)-2-((2-(trimethylsilyl)ethoxy)methyl)propane-1,3-diol (0.312 g, overall yield: 87%) was obtained in the same way as in Reference Example 5 by using 2-(chloromethoxy)ethyltrimethylsilane (0.210 mL, 1.18 mmol) instead of 1-bromodecane.

ESI-MS m/z: 455 (M+H)$^+$

Step 2

2-((9Z,12Z)-Octadeca-9,12-dien-1-yl)-2-((2-(trimethylsilyl)ethoxy)methyl)propane-1,3-diol (0.312 g, 0.686 mmol) obtained in step 1 was dissolved in tetrahydrofuran (4 mL). To the solution, sodium hydride (60% oil, 0.063 g, 1.58 mmol) and (9Z,12Z)-octadeca-9,12-dienyl methanesulfonate (0.355 g, 1.03 mmol) were added under ice cooling, and the mixture was stirred at 60° C. for 2 hours. A saturated aqueous solution of ammonium chloride was added to the reaction mixture, and the aqueous layer was extracted with hexane. The organic layer was washed with saturated saline, dried over anhydrous magnesium sulfate, then filtered and concentrated under reduced pressure. The obtained residue was purified by silica gel column chromatography (hexane/ethyl acetate=99/1 to 70/30) to obtain (11Z,14Z)-2-((((9Z,12Z)-octadeca-9,12-dien-1-yl)oxy)methyl)-2-((2-(trimethylsilyl)ethoxy)methyl)icosa-11,14-dien-1-ol (0.230 g, yield: 48%).

ESI-MS m/z: 703 (M+H)$^+$

Step 3

(11Z,14Z)-2-((((9Z,12Z)-Octadeca-9,12-dien-1-yl)oxy)methyl)-2-((2-(trimethylsilyl)ethoxy)methyl)icosa-11,14-dien-1-ol (0.230 g, 0.327 mmol) obtained in step 2 was dissolved in dichloromethane (2 mL). To the solution, a boron trifluoride-diethyl ether complex (manufactured by Tokyo Chemical Industry Co., Ltd., 0.207 mL, 1.64 mmol) was added under ice cooling, and the mixture was stirred at 0° C. for 1 hour. A saturated aqueous solution of sodium bicarbonate was added to the reaction mixture, and the aqueous layer was extracted with ethyl acetate. The organic layer was washed with saturated saline, dried over anhydrous magnesium sulfate, then filtered and concentrated under reduced pressure. The obtained residue was purified by silica gel column chromatography (hexane/ethyl acetate=99/1 to 50/50) to obtain compound IIc-7 (0.150 g, yield: 76%).

ESI-MS m/z: 603 (M+H)$^+$

Example 20

1-Methyl-3-((9Z,12Z)-octadeca-9,12-dien-1-yl)-3-((((9Z,12Z)-octadeca-9,12-dien-1-yl)oxy)methyl) azetidine (Compound 20)

Compound 20 (0.080 g, yield: 58%) was obtained in the same way as in Example 1 by using compound IIc-7 (0.140 g, 0.232 mmol) obtained in Reference Example 8 instead of compound IIc-1 obtained in Reference Example 1.

ESI-MS m/z: 598 (M+H)$^+$; $^1$H-NMR (CDCl$_3$) δ: 0.89 (6H, t, J=7.0 Hz), 1.17-1.40 (34H, m), 1.52-1.61 (4H, m), 2.02-2.08 (8H, m), 2.30 (3H, s), 2.77 (4H, t, J=6.6 Hz), 2.90 (2H, d, J=7.6 Hz), 3.10 (2H, d, J=7.6 Hz), 3.39-3.45 (4H, m), 5.27-5.44 (8H, m).

Example 21

A composition was prepared as follows using Compound 1 obtained in Example 1. The nucleic acid used was anti-f7 siRNA silencing blood coagulation factor VII (hereinafter referred to as f7) gene and consisted of a sense strand [5'-rGrGrAfUfCrAfUfCfUfCrArArGfUfCfUfUrAfCdTdT-3' (sugars attached to the bases with r, d, and f are ribose, deoxyribose, and ribose with the hydroxy group at position 2' substituted with fluorine, respectively, and the bond between deoxyribose attached to the 20th base counted from the 5' end toward the 3' end and deoxyribose attached to the 21st base thus counted is a phosphorothioate bond)] and an antisense strand [5'-rGfUrArArGrAfCfUfUrGrArGrAfUr-GrAfUfCfCdTdT-3' (sugars attached to the bases with r, d, and f are ribose, deoxyribose, and ribose with the hydroxy group at position 2' substituted with fluorine, respectively, and the bond between deoxyribose attached to the 20th base counted from the 5' end toward the 3' end and deoxyribose attached to the 21st base thus counted is a phosphorothioate bond)]. This nucleic acid was obtained from GeneDesign, Inc. (hereinafter, referred to as f7 siRNA-1). The nucleic acid was used after being adjusted to 24 mg/mL with distilled water.

Each sample was weighed to be compound 1/PEG-DMPE Na (manufactured by NOF Corp.)=57.3/5.52 mmol/L, and suspended in an aqueous solution containing hydrochloric acid and ethanol. A homogenous suspension was obtained by repeating stirring with a vortex stirring mixer and heating. This suspension was passed through a 0.05-μm polycarbonate membrane filter at room temperature to obtain a dispersion of compound 1/PEG-DMPE Na particles (liposomes). The average particle size of the obtained liposomes was measured with a particle size measurement apparatus to confirm that the average particle size fell within the range of 30 nm to 100 nm. The obtained liposome dispersion and the f7 siRNA-1 solution were mixed at a ratio of liposome dispersion:f7 siRNA-1 solution=3:1. A 3-fold amount of distilled water was further added thereto and mixed to prepare a compound 1/PEG-DMPE Na/f7 siRNA-1 complex dispersion.

Meanwhile, each sample was weighed to be compound 1/PEG-DMPE Na (manufactured by NOF Corp.)/DSPC (manufactured by NOF Corp.)/cholesterol (manufactured by NOF Corp.)=8.947/0.147/5.981/14.355 mmol/L, and dissolved in ethanol to prepare a lipid membrane constituent solution.

The obtained lipid membrane constituent solution and the obtained compound 1/PEG-DMPE Na/f7 siRN-1 complex dispersion were mixed at a ratio of 1:1 and further mixed with a several-fold amount of distilled water to obtain a crude preparation.

The obtained crude preparation was concentrated using Amicon Ultra (manufactured by Merck Millipore), then diluted with physiological saline and filtered using a 0.2-μm filter (manufactured by Toyo Roshi Kaisha, Ltd.) in a clean bench. The siRNA concentration of the obtained composition was measured, and the composition was diluted with physiological saline according to an administration concentration to obtain a preparation (composition containing compound 1 and f7 siRNA-1).

Example 22

Preparations (compositions containing compounds 2 and 4 to 7, respectively, and f7 siRNA-1) were obtained in the same way as in Example 21 using compounds 2 and 4 to 7, respectively, which are the compounds obtained in Examples 2 and 4 to 7.

The average particle sizes of the preparations (compositions) obtained in Examples 21 and 22 were measured using a particle size measurement apparatus. The results are shown in Table 4.

TABLE 4

| | Compound No. | | | | | |
|---|---|---|---|---|---|---|
| | 1 | 2 | 4 | 5 | 6 | 7 |
| Particle size of obtained preparation (nm) | 113 | 116 | 127 | 115 | 123 | 128 |

Example 23

A preparation was prepared in the same way as in Example 21 except that f7 siRNA-1 used in Example 21 was changed to f7 siRNA-2 having 5'-CCCUGUCUUGGUUU-CAAUUAA-3' (all sugars attached to the bases are ribose) as a sense strand and 5'-AAUUGAAACCAAGACA-GGGUG-3' (all sugars attached to the bases are ribose; the 5' end is modified with a phosphoric acid group) as an antisense strand.

Comparative Example 1

A preparation was prepared in the same way as in Example 23 except that compound 1 was changed to 1-methyl-3,3-bis{[(9Z,12Z)-octadeca-9,12-dien-1-yloxy]methyl}azetidine (compound A) synthesized by a method equivalent to the method described in Patent Literature 3.

The average particle sizes of the preparations (compositions) obtained in Example 23 and Comparative Example 1 were measured using a particle size measurement apparatus. The results are shown in Table 5.

TABLE 5

| | Example 23 | Comparative Example 1 |
|---|---|---|
| Particle size of obtained preparation (nm) | 119 | 140 |

Test Example 1

The preparations (compositions containing compounds 1, 2, and 4 to 7, respectively, and f7 siRNA-1) obtained in Examples 21 and 22 were each subjected to an in vivo drug efficacy evaluation test by a method given below. Each preparation was used after being diluted with physiological saline according to the test.

Mice (Balb/c, obtained from CLEA Japan, Inc.) were acclimatized and raised. Then, each preparation was intravenously administered at 0.03 and/or 0.3 mg/kg in terms of the siRNA concentration to the mice. 48 hours after the administration, blood was collected, and the collected blood was centrifuged at 8000 rpm at 4° C. for 8 minutes using a high-speed refrigerated microcentrifuge (TOMY MX305; manufactured by Tomy Seiko Co., Ltd.). Absorbance in standard solutions and the plasma samples was measured in ARVO (405 nm) using BIOPHEN VII kit (manufactured by ANIARA, cat#: A221304) according to the method described in the instruction manual of the product. A calibration curve was prepared from the obtained absorbance, and the factor VII protein concentration in plasma was calculated. n=3 for each group.

The results about the calculated factor VII protein concentration in plasma are shown in FIGS. 1 and 2.

Test Example 2

Test Example 2 was carried out in the same way as in Test Example 1 except that the preparations obtained in Examples 21 and 22 were changed to the preparations obtained in Example 23 and Comparative Example 1.

The results about the calculated factor VII protein concentration in plasma are shown in FIG. 3.

As is evident from FIGS. 1 and 2, the expression of the factor VII gene was strongly suppressed by the administration of each the preparations (compositions containing compounds 1, 2, and 4 to 7, respectively, and f7 siRNA-1) obtained in Examples 21 and 22.

Also, as is evident from FIG. 3, the expression of the factor VII gene was more strongly suppressed by the preparation (composition containing compound 1 and f7 siRNA-2) obtained in Example 23 than the preparation (composition containing compound A and f7 siRNA-2) obtained in Comparative Example 1.

These results demonstrated that the composition of the present invention can introduce a nucleic acid into a cell or the like, and the cationic lipid of the present invention facilitates delivering a nucleic acid into a cell in vivo.

INDUSTRIAL APPLICABILITY

A composition containing the cationic lipid of the present invention and a nucleic acid can easily introduce the nucleic acid, for example, into a cell, by its administration to a mammal or the like.

FREE TEXT OF SEQUENCE LISTING

SEQ ID NO: 1-blood coagulation factor VII siRNA-1 sense strand

SEQ ID NO: 2-blood coagulation factor VII siRNA-1 antisense strand

SEQ ID NO: 3-blood coagulation factor VII siRNA-2 sense strand

SEQ ID NO: 4-blood coagulation factor VII siRNA-2 antisense strand

The invention claimed is:

1. A cationic lipid of the formula (I″):

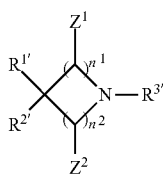

wherein $R^{1'}$ and $R^{2'}$ are, the same or different, linear, alkenyl, having 12 to 24 carbon atoms;

$R^{3'}$ is alkyl having 1 to 3 carbon atoms.

2. The cationic lipid according to claim 1, wherein $R^{1'}$ and $R^{2'}$ are, the same or different, selected from the group consisting of (Z)-tetradec-9-enyl, (Z)-hexadec-9-enyl, (Z)-octadec-6-enyl, (Z)-octadec-9-enyl, (E)-octadec-9-enyl, (Z)-octadec-11-enyl, (9Z,12Z)-octadeca-9,12-dienyl, (9Z,12Z,15Z)-octadeca-9,12,15-trienyl, (Z)-icos-11-enyl, (11Z,14Z)-icosa-11,14-dienyl, and (Z)-docos-13-enyl.

3. The cationic lipid according to claim 1, wherein $R^{1'}$ and $R^{2'}$ are, the same or different, selected from the group consisting of (Z)-hexadec-9-enyl, (Z)-octadec-9-enyl, (9Z,12Z)-octadeca-9,12-dienyl, and (11Z,14Z)-icosa-11,14-dienyl.

4. The cationic lipid according to claim 1, wherein $R^{1'}$ and $R^{2'}$ are the same.

5. A composition comprising the cationic lipid according to claim 1 and a nucleic acid.

6. The composition according to claim 5, wherein the cationic lipid and the nucleic acid form a complex, or the cationic lipid combined with a neutral lipid and/or a polymer and the nucleic acid form a complex.

7. The composition according to claim 5, wherein the cationic lipid and the nucleic acid form a complex, or the cationic lipid combined with a neutral lipid and/or a polymer and the nucleic acid form a complex, and the composition contains a lipid membrane with which the complex is enclosed.

8. The composition according to claim 5, wherein the nucleic acid is a nucleic acid having a silencing effect on a target gene through the use of RNA interference (RNAi).

9. The composition according to claim 8, wherein the target gene is a gene expressed in the liver, the lung, the kidney, or the spleen.

10. A therapeutic agent for a disease related to the liver, the lung, the kidney, or the spleen, comprising a composition according to claim 9.

11. The therapeutic agent for a disease related to the liver, the lung, the kidney, or the spleen according to claim 10, wherein the therapeutic agent is for intravenous administration.

12. A medicament for use in the treatment of a disease, comprising a composition according to claim 8.

13. The medicament according to claim 12, wherein the medicament is for intravenous administration.

* * * * *

UNITED STATES PATENT AND TRADEMARK OFFICE
CERTIFICATE OF CORRECTION

| | | |
|---|---|---|
| PATENT NO. | : 10,500,158 B2 | Page 1 of 1 |
| APPLICATION NO. | : 15/322271 | |
| DATED | : December 10, 2019 | |
| INVENTOR(S) | : Hosoe et al. | |

It is certified that error appears in the above-identified patent and that said Letters Patent is hereby corrected as shown below:

In the Claims

In Column 65, Line 65, Claim 1, "$R^{3'}$ is alkyl having 1 to 3 carbon atoms." should read
--$R^{3'}$ is alkyl having 1 to 3 carbon atoms;
$n^1$ is 1; $n^2$ is 1;
$Z^1$ is a hydrogen atom; and
$Z^2$ is a hydrogen atom.--

Signed and Sealed this
Seventeenth Day of March, 2020

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 21
<212> TYPE: DNA
```

<213> ORGANISM: Artificial Sequence
<220> FEATURE:
<223> OTHER INFORMATION: Blood Coagulation Factor VII siRNA -1 sense
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (4)..(4)
<223> OTHER INFORMATION: n = uracil
<220> FEATURE:
<221> NAME/KEY: misc_feature
<222> LOCATION: (7)..(7)
<223> OTHER INFORMATION: n = uracil
<220> FEATURE:
<221> NAME/KEY: misc_feature
<222> LOCATION: (9)..(9)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (16)..(17)
<223> OTHER INFORMATION: n = uracil
<220> FEATURE:
<221> NAME/KEY: modified_base
<222> LOCATION: (4)..(5)
<223> OTHER INFORMATION: 2'-fluoro
<220> FEATURE:
<221> NAME/KEY: modified_base
<222> LOCATION: (7)..(10)
<223> OTHER INFORMATION: 2'-fluoro
<220> FEATURE:
<221> NAME/KEY: modified_base
<222> LOCATION: (14)..(17)
<223> OTHER INFORMATION: 2'-fluoro
<220> FEATURE:
<221> NAME/KEY: modified_base
<222> LOCATION: (19)..(19)
<223> OTHER INFORMATION: 2'-fluoro
<220> FEATURE:
<221> NAME/KEY: misc_feature
<222> LOCATION: (21)..(21)
<223> OTHER INFORMATION: 5'-phosphorothioated Thymidine

<400> SEQUENCE: 1
ggancancnc aagncnnact t                                              21

<210> SEQ ID NO 2
<211> LENGTH: 21
<212> TYPE: DNA
<213> ORGANISM: Artificial Sequence
<220> FEATURE:
<223> OTHER INFORMATION: Blood Coagulation Factor VII siRNA -1 antisense
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (2)..(2)
<223> OTHER INFORMATION: n = uracil
<220> FEATURE:
<221> NAME/KEY: misc_feature
<222> LOCATION: (8)..(9)
<223> OTHER INFORMATION: n = uracil
<220> FEATURE:
<221> NAME/KEY: misc_feature
<222> LOCATION: (14)..(14)
<223> OTHER INFORMATION: n = uracil
<220> FEATURE:
<221> NAME/KEY: misc_feature
<222> LOCATION: (17)..(17)
<223> OTHER INFORMATION: n = uracil

```
<220> FEATURE:
<221> NAME/KEY: modified_base
<222> LOCATION: (2)..(2)
<223> OTHER INFORMATION: 2'-fluoro
<220> FEATURE:
<221> NAME/KEY: modified_base
<222> LOCATION: (7)..(9)
<223> OTHER INFORMATION: 2'-fluoro
<220> FEATURE:
<221> NAME/KEY: modified_base
<222> LOCATION: (14)..(14)
<223> OTHER INFORMATION: 2'-fluoro
<220> FEATURE:
<221> NAME/KEY: modified_base
<222> LOCATION: (17)..(19)
<223> OTHER INFORMATION: 2'-fluoro
<220> FEATURE:
<221> NAME/KEY: misc_feature
<222> LOCATION: (21)..(21)
<223> OTHER INFORMATION: 5'-phosphorothioated Thymidine

<400> SEQUENCE: 2
gnaagacnng agangancct t                                             21

<210> SEQ ID NO 3
<211> LENGTH: 21
<212> TYPE: RNA
<213> ORGANISM: Artificial Sequence
<220> FEATURE:
<223> OTHER INFORMATION: Blood Coagulation Factor VII siRNA -2 sense

<400> SEQUENCE: 3
cccugucuug guuucaauua a                                             21

<210> SEQ ID NO 4
<211> LENGTH: 21
<212> TYPE: RNA
<213> ORGANISM: Artificial Sequence
<220> FEATURE:
<223> OTHER INFORMATION: Blood Coagulation Factor VII siRNA -2 antisense
<220> FEATURE:
<221> NAME/KEY: misc_feature
<222> LOCATION: (1)..(1)
<223> OTHER INFORMATION: 5'-O-phosphorylated Adenine

<400> SEQUENCE: 4
nauugaaacc aagacagggu g                                             21
```